United States Patent
Zaferan et al.

(10) Patent No.: US 11,571,405 B2
(45) Date of Patent: Feb. 7, 2023

(54) COMPOSITIONS FOR IMPROVING SEXUAL FUNCTION

(71) Applicant: INXO A/S, Copenhagen (DK)

(72) Inventors: Djamaluddin Zaferan, Copenhagen (DK); Jahangir Khan, Copenhagen (DK)

(73) Assignee: INXO A/S, Copenhagen (DK)

( * ) Notice: Subject to any disclaimer, the term of this patent is extended or adjusted under 35 U.S.C. 154(b) by 0 days.

(21) Appl. No.: 17/504,255

(22) Filed: Oct. 18, 2021

(65) Prior Publication Data

US 2022/0040132 A1 Feb. 10, 2022

Related U.S. Application Data

(60) Division of application No. 17/056,290, filed on Nov. 17, 2020, now Pat. No. 11,304,920, and a continuation-in-part of application No. 16/706,087, filed as application No. PCT/EP2019/083983 on Dec. 6, 2019, now Pat. No. 10,993,924.

(30) Foreign Application Priority Data

Dec. 7, 2018 (DK) .......................... PA 2018 70801

(51) Int. Cl.
 *A61K 31/198* (2006.01)
 *A61K 31/352* (2006.01)
 *A61P 15/00* (2006.01)

(52) U.S. Cl.
 CPC .......... *A61K 31/198* (2013.01); *A61K 31/352* (2013.01); *A61P 15/00* (2018.01)

(58) Field of Classification Search
 CPC ...... A61K 31/198; A61K 31/352; A61P 15/00
 See application file for complete search history.

(56) References Cited

U.S. PATENT DOCUMENTS

| | | | |
|---|---|---|---|
| 9,572,848 | B1 | 2/2017 | Vascoe et al. |
| 2004/0062680 | A1 | 4/2004 | Kampa |
| 2013/0164394 | A1 | 6/2013 | Ferrari |
| 2016/0038458 | A1 | 2/2016 | Benckini |

FOREIGN PATENT DOCUMENTS

| | | | | |
|---|---|---|---|---|
| CA | 2967587 A1 | * | 4/2009 | ............... A23L 2/52 |
| CN | 101780181 | | 7/2010 | |
| CN | 103263018 | | 8/2013 | |
| CN | 104382892 | | 3/2015 | |
| EP | 1754478 | | 2/2007 | |
| EP | 2585088 | | 6/2014 | |
| WO | 2006/002096 | | 1/2006 | |
| WO | 2011161655 | | 12/2011 | |
| WO | 2017040421 | | 3/2017 | |

OTHER PUBLICATIONS

Chu, L., et al., "Handbook of Dual-effect Self-treatment of Sexual Dysfunction," Liaoning Science and Technology Press (1st Ed.), 2002 pp. 38-39.
Cormio, L., et al., "Oral L-Citrulline Supplementation Improves Erection Hardness in Men with Mild Erectile Dysfunction," Urology, 77 (1), 2011, pp. 119-122.
Stanislavov et al., "Improvement of erectile function with Prelox: a randomized, double-blind, placebo-controlled crossover trial", International Journal of Impotence Research, 2008, vol. 20, pp. 173-180.
Stanislavov et al., "Treatment of Erectile Dysfunction with Pycnogenol and L-arginine", Journel of Sex & Marital Therapy, 2003, vol. 29, Issue 3, pp. 207-213.
Abstract of Bottari, A., et al., "Lady Prelox improves sexual function in generally healthy women of reproductive age," Minerva Ginecologica, Aug. 2013; 65(4): 435-444.
Stanislavov et al., "Treatment of Erectile Dysfunction with Pycnogenol and L-arginine", Journel of Sex & Marital Therapy, 2003, vol. 29, Issue 3, pp. 207-213.
Klotz et al., "Effectiveness of Oral L-Arginine in First-Line Treatment of Erectile Dysfunction in a Controlled Crossover Study", Urol Int, 1999, vol. 63, pp. 220-223.
Stanislavov, R., et al., "Improvement of erectile function by a combination of French maritime pine bar and roburins with aminoacids" Minerva Urol Nefrol, 2015;67:27-32.
D'Andrea, G., "Pycnogenol: A blend of procyanidins with multi-faceted therapeutic applications?", Fitoterapia 81(2010) 724-736.
Suzuki, et al., Bioscience, Biotechnology and Biochemistry, 2017, vol. 81, No. 2, pp. 372-375.

\* cited by examiner

*Primary Examiner* — San Ming R Hui
(74) *Attorney, Agent, or Firm* — Duane Morris LLP; Gregory M. Lefkowitz; Brandon A. Chan

(57) ABSTRACT

Compositions comprising L-arginine and L-citrulline in specific ratios are provided. Use of such compositions for improving sexual function in a healthy human subject are also provided.

3 Claims, No Drawings

US 11,571,405 B2

COMPOSITIONS FOR IMPROVING SEXUAL FUNCTION

CROSS-REFERENCE TO RELATED APPLICATIONS

This application is a divisional application of U.S. patent application Ser. No. 17/056,290, filed on Nov. 17, 2020, which is a § 371 national stage entry of International Patent Application No. PCT/EP2019/083983, filed on Dec. 6, 2019, which claims priority to Danish Patent Application No. PA 2018 70801, filed on Dec. 7, 2018, and U.S. patent application Ser. No. 17/056,290 is also a continuation in part application of U.S. patent application Ser. No. 16/706,087, filed on Dec. 6, 2019, now U.S. Pat. No. 10,993,924, the entire contents of which are incorporated herein by reference.

FIELD OF THE INVENTION

The present invention relates to compositions comprising L-arginine and L-citrulline in specific ratios and the use thereof. In particular, the present invention relates to the use of such compositions for improving the sexual function in a sexually healthy human subject on demand.

BACKGROUND OF THE INVENTION

Sexuality is a complex interplay of multiple facets, including anatomical, physiological, psychological, developmental, cultural, and relational factors. All of these contribute to an individual's sexuality in varying degrees at any point in time as well as developing and changing throughout the life cycle.

Several sexual disorders and dysfunctions such as erectile dysfunction (ED), sexual arousal disorder, hypoactive sexual desire disorder (HSDD), sexual aversion disorder (SAD), orgasmic disorder (anorgasmia), premature ejaculation, dyspareunia, vaginismus or sexual dissatisfaction (non-specific) impair a natural healthy sexuality and may be caused by both physiological factors (e.g. insufficient hormone levels, diabetes, cardiovascular diseases or age) and psychological factors. Lack of sufficient amounts of sex hormones is a major factor influencing sexual motivation in both men and woman. Such hormones include androgens (e.g. testosterone), estrogens (e.g. estradiol), progestogens (e.g. progesterone), oxytocin and vasopressin. In women, lack of estrogen may lead to sexual dysfunction, primarily by causing vaginal atrophy and dyspareunia. These symptoms may be treated by systemic or local estrogen therapy. Conversely, androgen deficiency appears to be most strongly linked to diminished sexual desire. Growing evidence indicates that administration of androgens may be beneficial in such situations.

Penile erection is controlled by the body by two distinct mechanisms: the reflex erection, which is achieved by direct stimulation, and the psychogenic erection, which is achieved by erotic or emotional stimuli. The former uses the peripheral nerves and the lower parts of the spinal cord, whereas the latter uses the limbic system of the brain. In both cases, an intact neural system is required for a successful and complete erection. Direct stimulation of the nervous system in the penile shaft leads to the secretion of nitric oxide (NO). This secondary messenger causes relaxation of smooth muscles of corpora cavernosa (the main erectile tissue of penis), and subsequently penile erection. Nitric oxide functions by binding to the heme moiety of cytosolic guanylate cyclase, activating guanylate cyclase and increasing intracellular levels of cyclic guanosine monophosphate (cGMP). cGMP in turn relaxes vascular smooth muscle in blood vessels, which leads to vasodilation and increased blood flow both necessary to maintain erectile function. The current first-line therapeutic class for ED is phosphodiesterase type-5 inhibitors (PDE-5 inhibitors), preventing the metabolism of cGMP, prolonging the action of this second messenger on the vascular smooth muscle. Increasing blood flow in female genital tissue is also useful to improve sexual wellness. However, PDE5 inhibitors such as sildenafil (Viagra®) do not increase circulation to genital tissue in women as drastically as in men.

Another way to increase the blood flow into the female or male sexual organs is to increase the production of nitric oxide, which in turn triggers the release of cGMP. Whereas sildenafil and related substances lead to a sustained increase of blood content of the male or female sexual organs by blocking the enzymatic destruction of the vasodilating cGMP, nitric oxide produces the same increased blood volume by enhancing the production of cGMP.

Nitric oxide (NO) is biosynthesized endogenously from L-Arginine, oxygen and NADPH by various nitric oxide synthase (NOS) enzymes. The NOS enzymes convert L-Arginine into L-Citrulline and NO using $O_2$ as terminal oxidant. Thus, the production of NO is dependent of sufficient availability of L-Arginine as substrate. Several publications (e.g. Urol Int. 1999; 63(4):220-3./J Sex Marital Ther. 2003 May-June; 29(3):207-13./Int J Impot Res. 2008 March-April; 20(2):173-80. Epub 2007 Aug. 16) have shown the beneficial effect of administering L-Arginine to a person suffering from ED. L-Arginine may also be synthesized endogenously from L-citrulline by the sequential action of the two enzymes argininosuccinate synthetase and argininosuccinate lyase. Both these enzymes play important roles in the urea cycle. Several publications (e.g. Urology. 2011 January; 77(1): 119-22) show beneficial effects of administration of L-citrulline in patients suffering from ED although less effective than PDE-5 inhibitors. L-citrulline shows higher bioavailability than L-Arginine, mainly due to less exposure of presystemic metabolism as compared to L-Arginine.

Several attempts to develop compositions for use in the treatment of a sexual dysfunction or disorder, by stimulating NO production, have been disclosed in prior art. As an example, EP 2 585 088 discloses compositions consisting of an L-arginine source, proanthocyanidins from a plant extract and a Rose hip and/or *Quercus robur* extract. These compositions are intended for continuous treatment with a daily dosage regimen to treat a sexual disorders and/or dysfunction.

US 2004/062680 A1 discloses compositions comprising arginine and proanthocyanidins for attaining sexual wellness and health of the sexual vascular system. The sexual wellness or sexual fitness is enhanced over time by administrating a source of proanthocyanidins and a source of arginine on a daily basis. The source of L-arginine may be an L-arginine salt or a peptide of L-arginine, such as arginine aspartate. A sufficient amount of the nitric oxide is released over time to enhance sexual wellness or sexual fitness.

EP 2 585 088 B1 and WO11161655 A1 describes compositions for improving sexual fitness or wellness of both sexes comprising a source of proanthocyanidins, a source of arginine and rose hip and/or extracts thereof or *Quercus robur* and/or extracts thereof administered at a dosage of between 5 mg per day to 2000 mg per day. A composition referred to as Prelox Lady® comprising 20 mg Pycnogenol®, 200 mg L-arginine, 200 mg L-citrulline and 50 mg rose hip extract is described. This composition is intended for long term treatment of sexually dysfunctional women.

WO 2017040421 A1 describes a composition comprising about 5 mg-1000 mg of L-arginine and L-citrulline or a combination thereof. Preferably, L-arginine and L-citrulline are present in the composition at a weight range from 1:1 to 5:1 and L-arginine and L-citrulline each comprise from 1 to 80 wt % of the composition. The composition is disclosed as being used for the treatment of erectile dysfunction and premature ejaculation.

CN103263018 A describe a functional drink comprising per 1000 ml; 4 g L-arginine, 0.4 g L-citrulline acid, 60 mg vitamin C, 12 mg vitamin E, 0.2 mg folic acid, 30 mg beta-carotene, 30 mg alpha-lipoic acid and 300 mg taurine.

CN104382892 A describes a daily intake of a composition comprising 4-6 g of L-arginine, 200-1000 mg of L-citrulline, 300-500 mg of vitamin C and 20-30 mg of beta-carotene.

U.S. Pat. No. 9,572,848 B1 describes a slow release composition comprising 2000-4000 mg L-arginine, 1000-2000 mg L-citrulline, 1000-2000 mg L-carnitine, 10-40 mg zinc and 100-400 mg magnesium. The composition is for long term (at least 30 days) administration for treatment of female sexual arousal disorder, female orgasmic disorder and hypoactive sexual desire disorder or male erectile dysfunction.

US 2016/0038458 A1 describe the treatment of erectile dysfunction using a combination of mechanical and chemical treatment. The recommended chemical treatment is a continuous treatment comprising a dose of 3000-6000 mg arginine and 3000 mg citrulline daily taken as 2 doses e.g. one in the morning and one in the evening.

However, a drawback of the above treatments with daily dosage regimens is the side effects experienced and the need for continuous intake of medicine. Furthermore, compositions wherein the effect is based on plant extracts comprise complex mixtures of compounds some of which may not be beneficial to human health. Such compositions inevitably differ in dosage strength of the active ingredients due to variability between plant batches and/or species. In additions, the compositions in prior art mentioned above are mainly directed at erectile dysfunction as an alternative to prescription medicine such as sildenafil)(Viagra®). Thus, there is a need for improvement for further development of new compounds and compositions for the treatment of ED or more importantly for other sexual disorders or dysfunctions.

More importantly, however, there is a need for compositions for improving the sexual experiences of healthy human subjects on demand (non-continuous dosing). Healthy human subjects (i.e. not suffering from a sexual disorder or dysfunction) also have different degrees of sexual functioning (e.g. lust, desire or sexual fantasies) and improvements from the normal state are desired by many such subjects. Historically, such improvements have been sought by use of compounds and compositions referred to as "aphrodisiacs" or "love drugs" which are substances or compositions that increase libido when consumed. Aphrodisiacs are distinct from substances that address secondary sexual dysfunctions, such as e.g. erectile dysfunction.

Thus, there is still a need in the art for improving sexual function of sexually normally functioning subjects. Normally functioning subjects do not wish to be treated with medicaments. Especially, normally functioning subjects do not wish to be continuously (such as daily) treated or influenced by aphrodisiacs and/or medicaments (e.g. due to side effects). Hence, there is a need for compositions for use on demand (i.e. a need for compositions that are effective within a short time (0.5-4 hours) after a single intake), i.e. to increase their sexual experiences prior to planned sexual activities.

Especially, there is a need in the art for improving sexual function in normally functioning female subjects. Further, there is a need in the art for compositions that increase libido (e.g. psychological parameters such as sexual arousal) when consumed.

Even further there is a need in the art for compositions that increase libido while simultaneously increasing the physiological function, such as erectile and orgasmic function.

In particular, there is a need in the art for such compounds and compositions effecting female human subjects.

The present invention circumvents some of the drawbacks in the prior art compositions for the treatment of sexual disorders and dysfunctions. More importantly, the present invention solves the problem of providing a composition for on demand use as an aphrodisiac in a healthy subject having a normal sexual functioning.

Definitions

In the present context, an aqueous solution should be understood as any solution wherein at least 90% (V/V) of the solvent is water. Thus, an aqueous solution may also comprise other co-solvents such as EtOH or glycerol. In a preferred embodiment, the aqueous solution comprises water as the only solvent.

In the present context, treatment should be understood in the broadest sense. Thus, the term "treatment" is also intended to include relieving or ameliorating any symptoms (physiological or psychological) caused by a sexual disorder or dysfunction.

In the present context, the term "unit dosage" should be understood as a single dosage comprising an amount of active ingredients large enough to achieve a desired therapeutic response prior to sexual activity. Thus, a unit dosage is not intended for continuous treatment (i.e. such as a daily maintenance dose) but as a single loading dose needed prior to sexual activity.

In the present context, the term "sexual disorder or dysfunction" has the usual meaning in the art and may include but is not limited to endothelial dysfunction, erectile dysfunction, sexual arousal disorder, hypoactive sexual desire disorder (HSDD), sexual aversion disorder (SAD), orgasmic disorder (anorgasmia), premature ejaculation, dyspareunia, vaginismus and/or sexual dissatisfaction (non-specific). A sexual disorder or dysfunction has a negative impact on the sexual function or the sexual experience.

In the present context, the term "sexually healthy human subject" has the usual meaning in the art and refer to subjects having a normal sexual function, i.e. who do not suffer from a diagnosed (e.g. self-diagnosed) "sexual disorder or dysfunction".

In the present context, the term "sexual function" has the usual meaning in the art. Thus, sexual function refers to how the body reacts in different stages of the sexual response cycle. The human sexual response cycle is a four-stage model of physiological responses to sexual stimulation (mental or physiological), which, in order of their occurrence, are the excitement phase, plateau phase, orgasmic phase and resolution phase.

The sexual experience is strongly linked to a sexual function in an individual. In the present context, an "improved sexual function" and "improved sexual experience" may be equated and used interchangeably. Thus, in the present context an "improved sexual function and/or experience" may refer to the improvement in any physiological or psychological conditions, stimuli or characteristics present in any sexual related activity in a human subject, as well as a general improvement in wellness or pleasure during sexual activity. Improved sexual function/experience may be assessed by sexual arousal score, lubrication score, orgasm score, emotional satisfaction score, discomfort during penetration score, intercourse in general score, erection hardness score, de-sensitivity to penis score and/or IELT score.

In the present context, the term "sexual arousal" has the usual meaning in the art and refers to the state of mind in a human subject prior to engaging in sexual activities. The excitement phase (also known as the arousal phase or initial excitement phase) is the first stage of the human sexual response cycle, which occurs as a result of physical or mental erotic stimuli, such as kissing, petting, or viewing erotic images that lead to sexual arousal.

In the present context, the term "orgasmic function" has the usual meaning in the art and refers to the ability of a human subject to reach the climax state of sexual activity. The orgasm occurs during the orgasm phase and is the conclusion of the plateau phase of the sexual response cycle.

In the present context, the term "IELT" has the usual meaning in the art and refers to the intravaginal ejaculation latency time. IELT is the time taken by a man to ejaculate during vaginal penetration.

Proanthocyanidins has the usual meaning in the art and is a class of polyphenols found in a variety of plants. Chemically, they are oligomeric flavonoids. The proanthocyanidins include the subgroups procyanidins, prodelphinidins and propelargonidins. Proanthocyanidins are homogeneous or heterogeneous polymers consisting of the monomer units catechin or epicatechin and their gallic acid esters, which are connected either by 4-8 or 4-6 linkages, to the effect that a great number of isomer proanthocyanidins exist. Typically, the proanthocyanidins oligomers have a chain length of 2-12 monomer units. Proanthocyanidins may be synthesized or extracted from a plant material. Non-limiting examples of plant material sources of proanthocyanidins include grape seeds, grape skin, pine barks, ginkgo leaves, peanuts, cocoa beans, tamarind, raspberries, currants (black), peanut, almond, apple, cranberry, blueberry, tea leaves. Preferably, the source of proanthocyanidin consisting of a plant extract is selected among a pine bark extract, a grape seed extract or an extract of apples, peanut skin, walnuts, pomegranates, raspberries, currants (black), blueberries, almonds, tea, hawthorn or cocoa or combination thereof. The proanthocyanidins may be extracted with any conventional method, such e.g. solvent extraction or supercritical fluid extraction with $CO_2$. Furthermore, the compounds may be purified to any desired degree of purity using conventional means and methods in the art, such as solvent/solvent extraction, affinity chromatography (normal phase or reverse phase), precipitation or crystallization. A commercial source comprising proanthocyanidins exists under the trade name Pycnogenol®.

This product is a French maritime pine bark extract and may be used as a source of proanthocyanidins according to the invention.

SUMMARY OF THE INVENTION

The present invention resides in compositions comprising specific ratios and doses of L-arginine and L-citrulline or a physiologically acceptable salt or hydrate of any one thereof and in particular to such compositions additionally comprising a source of proanthocyanidins. More particularly, the present invention relates primarily to the use of such compositions for improving the sexual function or the sexual experience in a healthy subject having a normal sexual function. Secondarily, the present invention relates to the use of such a composition as a medicament for treating a sexual disorder or dysfunction such as ED. The present inventors surprisingly found that compositions comprising the combination of the active ingredients L-arginine and L-citrulline in certain ratios and at specific dosages provide formulations that show surprisingly high synergistic effects in normal healthy human subjects, in particular women, as compared to the individual compounds alone as well as to other ratios and amounts of the active ingredients.

In particular it was found that the minimum amount of L-arginine for providing on demand effect exceeded 4.0 g and that the corresponding minimum amount of L-citrulline was at least 1.0 g. With regards to the maximum amount of the active ingredients it has been observed that the safe level for oral administration of L-arginine is 20 g per day, and that even higher levels have been tested in short-term studies without serious adverse effects. At levels above 20 g per day some adverse effects, most commonly diarrhea, have been seen. Corresponding tolerated levels have been observed for oral administration of L-citrulline.

The additional presence of a source of proanthocyanidins was found to significantly improve the surprising results. These compositions may thus be used, not only to treat a sexual disorder or dysfunction, but also more surprisingly to improve the sexual function in a healthy subject having a normal sexual functioning. Furthermore, a significant advantage is that these compositions do not require a daily dosing frequency, but only a single dose prior to sexual activity.

The invention thus relates in general to a method for improving sexual fitness or wellness or sexual enhancement of (sexually) healthy human subject of both sexes comprising administering, to a subject in need of improved sexual fitness or wellness or sexual enhancement, a composition according to the invention.

In particular, the inventive method relates to a method for improving sexual fitness or wellness or sexual enhancement of (sexually) healthy human subject of both sexes comprising administering, to a subject in need of improved sexual fitness or wellness or sexual enhancement a composition comprising L-arginine and L-citrulline or a physiologically acceptable salt or hydrate of any one thereof, wherein the content of L-arginine or a physiologically acceptable salt or hydrate thereof is at least 4.0 g and the content of L-citrulline or a physiologically acceptable salt or hydrate thereof is at least 1.0 g. Preferably, the composition also comprises one or more proanthocyanidins. Preferably, the composition are in a unit dosage form and the content of L-citrulline or a physiologically acceptable salt or hydrate thereof is in the range from 1.0-3.0 g.

Most preferably, the molar ratio of L-arginine:L-citrulline is in the range from 2.0:10.0.

The invention thus relates to a method for improving sexual fitness or wellness or sexual enhancement of (sexually) healthy human subject of both sexes comprising administering, to a subject in need of improved sexual fitness or wellness or sexual enhancement, a composition comprising L-arginine and L-citrulline or a physiologically acceptable salt or hydrate of any one thereof, wherein L-arginine and L-citrulline, are present in the composition, respectively, in a weight ratio of from 2.0:1 to 10.0:1, preferably in a range from in 2.2:1 to 5.8:1, and wherein the content of L-arginine is at least 4.0 g, such as in the range from 4.0-20 g, preferably in the range from 4.0-12.0 g, more preferably in the range from 4.0-8.0 g and the content L-citrulline or a physiologically acceptable salt or hydrate thereof is at least 1.0 g such as in the range from 1.0-5.0 g, such as in the range from 1.0-3.0 g preferably 1.2-2.1 g.

In a preferred aspect thereof, the compositions comprise a third component, said third component comprising an effective amount of a source of proanthocyanidins, preferably being present in an amount of at least 5 mg.

Preferably, the composition is administered on demand (non-continuously) as a unit dosage.

More preferably, the composition is administered on demand as a functional drink, or as a composition intended for providing a functional drink, in a volume of from 20 ml-500 ml, more preferably from 100 ml-400 ml, more preferably from 150 ml-300 ml, most preferably from 200-250 ml.

DETAILED DESCRIPTION OF THE INVENTION

The present invention resides in compositions that are beneficial for improving the overall wellness in a human being during and/or prior to sexual activity. Thus, the compositions are intended for use on demand prior to a planned sexual activity to achieve an extraordinary sexual experience or to ameliorate the symptoms caused by a sexual disorder or dysfunction. In other words, the compositions are suitable as an aphrodisiac or "love drug" that increases the libido (i.e. sex drive) in a human subject when consumed. Thus, an embodiment of the invention relates to the use of the composition as an aphrodisiac. Yet another embodiment of the invention relates to a method of improving sexuality and/or sexual functioning in a healthy human subject. The improved wellness obtained with compositions according to the invention may reside in a mixture of both physiological and psychological effects due to the complexity of the human sexuality. In one instance, the composition is intended to improve the sexual arousal, the emotional satisfaction, the intercourse in general or any combination thereof in both men and women. In another instance, the composition is intended to desensitize the penis to avoid premature ejaculation in men. In yet another instance, the composition is intended to increase vaginal lubrication, discomfort during penetration and improve the chance of reaching climax during sexual activity in a female.

Amount of L-Arginine, L-Citrulline and a Source of Proanthocyanidin.

In a preferred aspect of the invention, the invention relates to a unit dosage composition comprising L-arginine and L-citrulline in a weight ratio of from 2.0:1 to 10.0:1, wherein L-arginine is present in the unit dose in an amount exceeding 4 g, such as at least 5.0 g, such as at least 6.0 g, such as in the range from 4.0-20 g, preferably in the range from 5.0-20.0 g, such as in the range from 6.0-20 g, preferably in the range from 4.0-12.0 g, preferably in the range from 5.0-12.0 g, such as in the range from 6.0-12 g, more preferably being in the range from 4.0-10.0 g, even more preferably from 5.0-10.0 g, such as in the range from 6.0-10 g, such as from 5.0-8.0 g, most preferably from 5.5-7 g, even more preferably about 6 g and the content L-citrulline or a physiologically acceptable salt or hydrate thereof is at least 1.0 g, preferably at least 1.5 g such as in the range from 1.0-5.0 g, such as in the range from 1.0-3.0 g, even more preferably from 1.0-2.1 g, such as from 1.5-2.1 g, more preferably 1.2-2.1 g.

Preferably, the ratio between L-arginine and L-citrulline is as disclosed below.

Preferably, the compositions according to the invention comprises a source of proanthocyanidin. The amount needed is limited as proanthocyanidin is believed to be a catalyst.

The compositions according to the invention may be formulated as a solid or powder composition for consumption directly.

However, the unit dosage compositions of the invention are preferably formulated as a functional drink, or, alternatively, formulated as a composition intended for mixing in a fluid composition for consumption said fluid composition having a volume of less than 500 ml. On demand unit dosage forms as functional drinks have a maximal total volume of about 500 ml. Larger volumes cannot be consumed on demand without impairing the purpose of the compositions according to the invention. Thus, preferably, the composition is provided for being administered on demand as a functional drink, or, alternatively, provided as a composition intended for providing a functional drink, said functional drink having a final volume of from 20 ml-500 ml, more preferably from 50 ml-400 ml, more preferably from 100 ml-300 ml, most preferably from 150-250 ml.

A preferred fluid for mixing with the composition according to the invention is fruit juice, in particular orange juice. Orange juice was found to mask the taste of the composition more satisfactorily than other juices. In case fruit juice is used it is preferred to add caffeine to the composition.

Another preferred fluid for mixing with the composition according to the invention is regular soft drinks, in particular lemon soda.

Ratio of L-Arginine to L-Citrulline

The inventors surprisingly found that L-arginine and L-citrulline in certain ratios provide synergistic effects compared to the individual compounds alone.

Thus, in a first aspect, the present invention relates to compositions comprising L-arginine and L-citrulline or a physiologically acceptable salt or hydrate of any one thereof in certain ratios. Hence, these compositions are useful for improving sexual function in a human being. Without being bound to theory, these compositions may aid in improving sexual function, e.g. by increasing the production of NO in situ. The inventors surprisingly found that the ratio of L-arginine and L-citrulline in the composition plays an essential role in improving the sexual function in male and females and that L-arginine must be in excess of L-citrulline. Thus an embodiment of the invention relates to compositions wherein the molar ratio of L-arginine:L-citrulline is in the range from 2.0:1 to 10.0:1, such as 2.0:1 to 9.0:1, such as 2.2:1 to 5.8:1, such as 2.4:1 to 5.6:1, such as 2.6:1 to 5.4:1, such as 2.8:1 to 5.2:1, such as 3:1 to 5.0:1, such as 3.2:1 to 4.8:1, such as 3.4:1 to 4.6:1, preferably 3.6:1 to 4.4:1, more preferably 3.8:1 to 4.2:1, most preferably 4:1. The molar ratio with an excess of L-arginine compared to L-citrulline is essential to achieve the synergistic effects with the compositions according to the invention.

The compositions according to the invention may be formulated by conventional means known to the person skilled in the art. In a preferred embodiment, the composition is a powder mixture suitable for dissolution and consumption prior to sexual activity. In a preferred embodiment, the powder mixture may be dissolved in a beverage such as a soft drink. In another preferred embodiment of the invention the composition is formulated as an aqueous solution that is intended for consumption on demand prior to sexual activity.

In an embodiment of the invention, the L-arginine content in the powder composition is typically in the range of 53-75% w/w, such as 55-73% w/w, such as 56-72% w/w, such as 57-71% w/w, such as 58-70% w/w, such as 59-69% w/w, such as 60-68% w/w, preferably 61-67% w/w, more preferably 62-66% w/w, even more preferably 63-65% w/w, most preferably 64% w/w.

In an embodiment of the invention, the L-citrulline content in the powder composition is typically in the range of 8-25% w/w, 10-22% w/w, 12-20% w/w, such as 12.5-19.5% w/w, such as 13-19% w/w, such as 13.5-18.5% w/w, such as 14-18% w/w, preferably 14.5-17.5% w/w, more preferably 15-17% w/w, even more preferably 15.5-16.5% w/w, most preferably 16% w/w.

Other Ingredients

Besides the essential ingredients L-arginine and L-citrulline, the inventors surprisingly found that further additives such as D-alpha-tocopherol, L-ascorbic acid, alpha-lipoic acid, folic acid, calcium and in particular one or more proanthocyanidins improved the effect of the composition (e.g. improved the sexual function in an individual). Thus, in an embodiment of the invention, the composition comprises L-arginine, L-citrulline and D-alpha-tocopherol or a physiologically acceptable salt or hydrate of any thereof. In an alternative embodiment of the invention, the composition comprises L-arginine, L-citrulline and at least one proanthocyanidin.

In a more preferred embodiment of the invention, the unit dosage comprises L-arginine, L-citrulline, D-alpha-tocopherol and a proanthocyanidin (a preferred source of proanthocyanidins is Pycnogenol®). In a more preferred embodiment of the invention, the unit dosage comprises L-arginine, L-citrulline, D-alpha-tocopherol, one or more proanthocyanidins and L-ascorbic acid. In an even more preferred embodiment of the invention, the unit dosage comprises L-arginine, L-citrulline, D-alpha-tocopherol, one or more proanthocyanidins, L-ascorbic acid and alpha-lipoic acid. In yet a more preferred embodiment of the invention, the unit dosage comprises L-arginine, L-citrulline, D-alpha-tocopherol, one or more proanthocyanidins, L-ascorbic acid, alpha-lipoic acid and folic acid. In the most preferred embodiment of the invention, the unit dosage comprises L-arginine, L-citrulline, D-alpha-tocopherol, one or more proanthocyanidins, L-ascorbic acid, alpha-lipoic acid, folic acid and calcium.

The inventors surprisingly found that proanthocyanidins are important for the activation of the compositions of the present invention comprising L-arginine and L-citrulline in certain ratios. The inventors also found that, with respect to the function, the proanthocyanidins seems to function as catalysers, and consequently, the amount of proanthocyanidins may be reduced substantially compared to the other ingredients. The one or more proanthocyanidins are preferably supplied to the compositions as a plant extract, preferably as a natural plant extract originating from the bark of a maritime pine that grows along the coast of southwest France (and e.g. sold under the tradename Pycnogenol®. When proanthocyanidins are supplied as Pycnogenol®, the preferred amount of Pycnogenol® in the powder compositions is preferably 6.9-101% w/w, such as 7.1-99% w/w, such as 7.3-97% w/w, such as 7.5-95% w/w, such as 7.7-93% w/w, preferably 7.9-91% w/w, more preferably 8.1-89% w/w, even more preferably 8.3-87% w/w, most preferably 10-80% w/w of the powder compositions.

The D-alpha-tocopherol in the powder composition is typically in the range of 0.8-2.4% w/w, such as 0.9-2.3% w/w, such as 1.0-2.2% w/w, such as 1.1-2.1% w/w, such as 1.2-2.0% w/w, preferably 1.3-1.9% w/w, more preferably 1.4-1.8% w/w, even more preferably 1.5-1.6% w/w, most preferably 1.4% w/w of the powder compositions.

The L-ascorbic acid in the powder composition is typically in the range of 3.7-6.9% w/w, such as 3.9-6.7% w/w, such as 4.1-6.5% w/w, such as 4.3-6.3% w/w, such as 4.5-6.1% w/w, preferably 4.7-5.9% w/w, more preferably 4.9-5.7% w/w, even more preferably 5.1-5.5% w/w, most preferably 5.3% w/w of the powder compositions.

The alpha-lipoic acid in the powder composition is typically in the range of 0.3-1.8% w/w, such as 0.3-1.7% w/w, such as 0.4-1.6% w/w, such as 0.5-1.5% w/w, such as 0.6-1.4% w/w, preferably 0.7-1.3% w/w, more preferably 0.8-1.2% w/w, even more preferably 0.9-1.1% w/w, most preferably 1% w/w of the powder compositions.

The folic acid in the powder composition is typically in the range of 0.01-0.07% w/w, such as 0.015-0.065% w/w, such as 0.02-0.06% w/w, preferably 0.025-0.055% w/w, more preferably 0.03-0.05% w/w, even more preferably 0.035-0.045% w/w, most preferably 0.04% w/w of the powder compositions.

The calcium in the powder composition is typically in the range of 5.7-8.1% w/w, such as 5.9-7.9% w/w, such as 6.1-7.7% w/w, preferably 6.3-7.5% w/w, more preferably 6.5-7.3% w/w, even more preferably 6.7-7.1% w/w, most preferably 6.9% w/w of the powder compositions.

Furthermore, the inventors surprisingly found that these compositions do not require daily dosing, as it suffices to administer a single dose prior to sexual activity.

Unit Dosage Compositions for on Demand Use

The inventors surprisingly found that compositions according to the present invention could be used by healthy human subjects as single dosage compositions (at relatively low dosages) avoiding the drawbacks of continuous treatment while providing the benefits of achieving improved sexuality on demand.

The inventors further surprisingly found that the same composition has comparable beneficial effects in improving sexual function in both sexes.

Thus, in a preferred embodiment of the invention, the composition is in a unit dosage form. The unit dosage may be in the form of a solid powder suitable for dissolution of a premixed drink for direct consumption. The unit dosage is intended as a suitable "on demand" dose that is taken prior to sexual activity to achieve a better sexual experience or ameliorate any symptoms caused by a sexual disorder or dysfunction.

Thus, the composition does not need to be taken following a predetermined dosage regimen (i.e. in predetermined time intervals) to maintain a certain blood plasma concentration of active substance, as is common for almost any medical treatment, i.e. it is not intended for continuous treatment. In other words, the individual human subject may tailor its consumption depending on its individual desire for sexual activity and desire for an extraordinary sexual experience ("on demand"). Thus, in a preferred embodiment of the invention, the compositions are intended for use by healthy human subjects that are not suffering from any sexual disorder or dysfunction (i.e. as an aphrodisiac). In another embodiment of the invention, the compositions are intended for use in the treatment of a human subject suffering from a diagnosed or self-diagnosed sexual dysfunction or disorder. Even in the latter case when the composition are used in the treatment of a sexual dysfunction or disorder a single dose may suffice prior to sexual activity, i.e. no continuous treatment is needed.

Accordingly, in an embodiment of the invention, the unit dosage comprises L-arginine and L-citrulline or physiologically acceptable salts or hydrates thereof in a (combined) amount in the range of from 6-14 g, such as 6.2-13.0 g, such as 6.4-12 g, such as 6.6-11 g, such as 6.8-10.0 g, such as 7.0-9.0 g, such as 7.2-8.0 g, preferably 7.5 g (as free amino acids). The skilled person would understand that the amounts may vary depending on the source of L-arginine and/or L-citrulline (e.g. salt and/or solvate). Thus, the skilled person is well aware that the amounts (e.g. L-arginine) may be expressed in mol instead and the amounts (g) calculated based on a salt and/or solvate with a higher molecular weight.

In an embodiment of the invention, the unit dosage comprises L-arginine or a physiologically acceptable salt or hydrate thereof is present in the unit dose in an amount exceeding 4 g, such as at least 5.0 g, such as at least 5.0 g, such as in the range from 4.0-20 g, preferably in the range from 5.0-20.0 g, such as in the range from 6.0-20 g, preferably in the range from 4.0-12.0 g, preferably in the range from 5.0-12.0 g, such as in the range from 6.0-12 g, more preferably being from 4.0-10.0 g, such as 4.4-9.5 g, such as 4.6-9.0 g, such as 4.8-8.0 g, even more preferably from 5.0-10.0 g, preferably 5.0-7.0 g, more preferably 5.2-6.8 g, even more preferably 5.4-6.6 g, 5.6-6.4 g, 5.8-6.2 g, preferably in the range from 6.0-10 g, such as from 5.0-8.0 g, most preferably from 5.5-7 g, even more preferably about 6 g, more preferably 6.0 g (34.4 mmol, free amino acid). The inventors found that 6.0 g of L-arginine was most efficacious, and that side effects occurred in some instances above 10 g (e.g. stomachache). Furthermore, higher amounts of L-arginine worsened the organoleptic properties of the unit dosage.

In an embodiment of the invention, the unit dosage comprises L-citrulline or a physiologically acceptable salt or hydrate thereof in the range from 0.5-3.0 g, such as 0.5-2.9 g, preferably 0.5-2.8 g, more preferably 0.5-2.7 g, such as 0.7-2.0 g, preferably 0.9-2.0 g, more preferably 1.1-2.0 g, even more preferably 1.3-2.0 g, most preferably 1.5-2.0 g. The inventors surprisingly found that the efficacy of a unit dosage was not improved further by L-citrulline in amounts above 2.0 g (i.e. plateau of efficacy). Furthermore, the inventors surprisingly found that a higher efficacy and potency of the composition was obtained when both L-arginine and L-citrulline were present. Particularly the composition was most efficacious when the amount of L-arginine was four times the amount of L-citrulline (i.e. 4:1 ratio). The inventors further found that the effect lasted longer and that a synergistic effect was obtained when both L-citrulline and L-arginine were present in the composition or unit dosage.

In an embodiment of the invention, the used unit dosage comprise L-arginine and L-citrulline or a physiologically acceptable salt or hydrate of any thereof, wherein the L-arginine or a physiologically acceptable salt or hydrate thereof in the range from 4-10 g, such as 4.4-9.5 g, such as 4.6-9.0 g, such as 4.8-8.0 g, preferably 5.0-7.0 g, more preferably 5.2-6.8 g, even more preferably 5.4-6.6 g, 5.6-6.4 g, 5.8-6.2 g, most preferably 6.0 g and the L-citrulline or a physiologically acceptable salt or hydrate thereof in the range from 0.5-3.0 g, such as 0.5-2.9 g, preferably 0.5-2.8 g, more preferably 0.5-2.7 g, such as 0.7-2.0 g, preferably 0.9-2.0 g, more preferably 1.1-2.0 g, even more preferably 1.3-2.0 g, most preferably 1.5-2.0 g.

In an embodiment of the invention, the unit dosage comprises D-alpha-tocopherol or a physiologically acceptable salt or hydrate thereof in the range from 85-185 mg, such as 90-180 mg, such as 95-175 mg, such as 100-170 mg, such as 105-165 mg, such as 110-160 mg, such as 115-155 mg, preferably 120-150 mg, more preferably 125-145 mg, even more preferably 130-140 mg, most preferably 133 mg.

In another embodiment of the invention, the unit dosage comprises L-arginine, L-citrulline and D-alpha-tocopherol or a physiologically acceptable salt or hydrate of any thereof, wherein the L-arginine or a physiologically acceptable salt or hydrate thereof in the range from 4-10 g, such as 4.4-9.5 g, such as 4.6-9.0 g, such as 4.8-8.0 g, preferably 5.0-7.0 g, more preferably 5.2-6.8 g, even more preferably 5.4-6.6 g, 5.6-6.4 g, 5.8-6.2 g, most preferably 6.0 g, the L-citrulline or a physiologically acceptable salt or hydrate thereof in the range from L-citrulline or a physiologically acceptable salt or hydrate thereof in the range from 0.5-3.0 g, such as 0.5-2.9 g, preferably 0.5-2.8 g, more preferably 0.5-2.7 g, such as 0.7-2.0 g, preferably 0.9-2.0 g, more preferably 1.1-2.0 g, even more preferably 1.3-2.0 g, most preferably 1.5 g and the D-alpha-tocopherol or a physiologically acceptable salt or hydrate thereof in the range from 85-185 mg, such as 90-180 mg, such as 95-175 mg, such as 100-170 mg, such as 105-165 mg, such as 110-160 mg, such as 115-155 mg, preferably 120-150 mg, more preferably 125-145 mg, even more preferably 130-140 mg, most preferably 133 mg.

In an embodiment of the invention, the unit dosage comprises one or more proanthocyanidins, preferably present as part of a plant extract, preferably as a natural plant extract originating from the bark of a maritime pine that grows along the coast of southwest France (and e.g. sold under the tradename Pycnogenol®). The one or more proanthocyanidins in the unit dosage are present in the range from 5-220 mg, such as 10-220 mg, such as 15-210 mg, such as 20-200 mg, such as 25-190 mg, such as 30-180 mg, such as 35-170 mg, such as 40-160 mg, preferably 50-140 mg, more preferably 60-120 mg, even more preferably 70-100 mg, most preferably 80 mg.

In a preferred embodiment of the invention, the unit dosage comprises L-arginine, L-citrulline and one or more proanthocyanidins, wherein the L-arginine or a physiologically acceptable salt or hydrate thereof in the range from 4-10 g, such as 4.4-9.5 g, such as 4.6-9.0 g, such as 4.8-8.0 g, preferably 5.0-7.0 g, more preferably 5.2-6.8 g, even more preferably 5.4-6.6 g, 5.6-6.4 g, 5.8-6.2 g, most preferably 6.0 g, the L-citrulline or a physiologically acceptable salt or hydrate thereof in the range from 0.5-3.0 g, such as such as 0.5-2.9 g, preferably 0.5-2.8 g, more preferably 0.5-2.7 g, 0.5-2.0 g, such as 0.7-2.0 g, preferably 0.9-2.0 g, more preferably 1.1-2.0 g, even more preferably 1.3-2.0 g, most preferably 1.5 g, and the proanthocyanidins in the range from 10-220 mg, such as 15-210 mg, such as 20-200 mg, such as 25-190 mg, such as 30-180 mg, such as 35-170 mg, such as 40-160 mg, preferably 50-140 mg, more preferably 60-120 mg, even more preferably 70-100 mg, most preferably 80 mg.

In another preferred embodiment of the invention, the unit dosage comprises L-arginine, L-citrulline, D-alpha-tocopherol and one or more proanthocyanidins, wherein the L-arginine or a physiologically acceptable salt or hydrate thereof in the range from 4-10 g, such as 4.4-9.5 g, such as 4.6-9.0 g, such as 4.8-8.0 g, preferably 5.0-7.0 g, more preferably 5.2-6.8 g, even more preferably 5.4-6.6 g, 5.6-6.4 g, 5.8-6.2 g, most preferably 6.0 g, the L-citrulline or a physiologically acceptable salt or hydrate thereof in the range from 0.5-3.0 g, such as 0.5-2.9 g, preferably 0.5-2.8 g, more preferably 0.5-2.7 g, such as 0.7-2.0 g, preferably 0.9-2.0 g, more preferably 1.1-2.0 g, even more preferably 1.3-2.0 g, most preferably 1.5-2.0 g, the D-alpha-tocopherol or a physiologically acceptable salt or hydrate thereof in the range from 85-185 mg, such as 90-180 mg, such as 95-175 mg, such as 100-170 mg, such as 105-165 mg, such as 110-160 mg, such as 115-155 mg, preferably 120-150 mg, more preferably 125-145 mg, even more preferably 130-140 mg, most preferably 133 mg and the one or more proanthocyanidins are present in the range from 10-220 mg, such as 15-210 mg, such as 20-200 mg, such as 25-190 mg, such as 30-180 mg, such as 35-170 mg, such as 40-160 mg, preferably 50-140 mg, more preferably 60-120 mg, even more preferably 70-100 mg, most preferably 80 mg.

In an embodiment of the invention, the unit dosage comprise L-ascorbic acid or a physiologically acceptable salt or hydrate thereof in the range from 300-700 mg, such as 320-680 mg, such as 340-660 mg, such as 360-640 mg, such as 380-620 mg, such as 400-600 mg, such as 420-580 mg, preferably 440-560 mg, more preferably 460-540 mg, even more preferably 480-520 mg, most preferably 500 mg.

In a more preferred embodiment of the invention, the unit dosage comprises L-arginine, L-citrulline, D-alpha-tocopherol, L-ascorbic acid and one or more proanthocyanidins, wherein L-arginine or a physiologically acceptable salt or hydrate thereof in the range from 4-10 g, such as 4.4-9.5 g, such as 4.6-9.0 g, such as 4.8-8.0 g, preferably 5.0-7.0 g, more preferably 5.2-6.8 g, even more preferably 5.4-6.6 g, 5.6-6.4 g, 5.8-6.2 g, most preferably 6.0 g, the L-citrulline or a physiologically acceptable salt or hydrate thereof in the range from 0.5-3.0 g, such as 0.5-2.9 g, preferably 0.5-2.8 g, more preferably 0.5-2.7 g, such as 0.7-2.0 g, preferably 0.9-2.0 g, more preferably 1.1-2.0 g, even more preferably 1.3-2.0 g, most preferably 1.5-2.0 g, the D-alpha-tocopherol or a physiologically acceptable salt or hydrate thereof in the range from 85-185 mg, such as 90-180 mg, such as 95-175 mg, such as 100-170 mg, such as 105-165 mg, such as 110-160 mg, such as 115-155 mg, preferably 120-150 mg, more preferably 125-145 mg, even more preferably 130-140 mg, most preferably 133 mg, the L-ascorbic acid or a physiologically acceptable salt or hydrate thereof in the range from 300-700 mg, such as 320-680 mg, such as 340-660 mg, such as 360-640 mg, such as 380-620 mg, such as 400-600 mg, such as 420-580 mg, preferably 440-560 mg, more preferably 460-540 mg, even more preferably 480-520 mg, most preferably 500 mg and one or more proanthocyanidins in the range from 10-220 mg, such as 15-210 mg, such as 20-200 mg, such as 25-190 mg, such as 30-180 mg, such as 35-170 mg, such as 40-160 mg, preferably 50-140 mg, more preferably 60-120 mg, even more preferably 70-100 mg, most preferably 80 mg.

In an embodiment of the invention, a unit dosage comprises alpha-lipoic acid or a physiologically acceptable salt or hydrate thereof is in the range from 5-15 mg, such as 5.5-14.5 mg, such as 6-14 mg, such as 6.5-13.5 mg, such as 7-13 mg, such as 7.5-12.5 mg, such as 8-12 mg, preferably 8.5-11.5 mg, more preferably 9-11 mg, even more preferably 9.5-10.5 mg, most preferably 10 mg.

In an even more preferred embodiment of the invention, the unit dosage comprises L-arginine, L-citrulline, D-alpha-tocopherol, L-ascorbic acid, alpha-lipoic acid one or more proanthocyanidins, wherein L-arginine or a physiologically acceptable salt or hydrate thereof in the range from 4-10 g, such as 4.4-9.5 g, such as 4.6-9.0 g, such as 4.8-8.0 g, preferably 5.0-7.0 g, more preferably 5.2-6.8 g, even more preferably 5.4-6.6 g, 5.6-6.4 g, 5.8-6.2 g, most preferably 6.0 g, the L-citrulline or a physiologically acceptable salt or hydrate thereof in the range from 0.5-3.0 g, such as 0.5-2.9 g, preferably 0.5-2.8 g, more preferably 0.5-2.7 g, such as 0.7-2.0 g, preferably 0.9-2.0 g, more preferably 1.1-2.0 g, even more preferably 1.3-2.0 g, most preferably 1.5-2.0 g, the D-alpha-tocopherol or a physiologically acceptable salt or hydrate thereof in the range from 85-185 mg, such as 90-180 mg, such as 95-175 mg, such as 100-170 mg, such as 105-165 mg, such as 110-160 mg, such as 115-155 mg, preferably 120-150 mg, more preferably 125-145 mg, even more preferably 130-140 mg, most preferably 133 mg, the L-ascorbic acid or a physiologically acceptable salt or hydrate thereof in the range from 300-700 mg, such as 320-680 mg, such as 340-660 mg, such as 360-640 mg, such as 380-620 mg, such as 400-600 mg, such as 420-580 mg, preferably 440-560 mg, more preferably 460-540 mg, even more preferably 480-520 mg, most preferably 500 mg, the alpha-lipoic acid or a physiologically acceptable salt or hydrate thereof is in the range from 5-15 mg, such as 5.5-14.5 mg, such as 6-14 mg, such as 6.5-13.5 mg, such as 7-13 mg, such as 7.5-12.5 mg, such as 8-12 mg, preferably 8.5-11.5 mg, more preferably 9-11 mg, even more preferably 9.5-10.5 mg, most preferably 10 mg and one or more proanthocyanidins in the range from 10-220 mg, such as 15-210 mg, such as 20-200 mg, such as 25-190 mg, such as 30-180 mg, such as 35-170 mg, such as 40-160 mg, preferably 50-140 mg, more preferably 60-120 mg, even more preferably 70-100 mg, most preferably 80 mg.

In an embodiment of the invention, the unit dosage comprises folic acid or a physiologically acceptable salt or hydrate thereof in the range from 200-600 mcg, such as 220-580 mcg, such as 240-560 mcg, such as 260-540 mcg, such as 280-520 mcg, such as 300-500 mcg, such as 320-480 mcg, preferably 340-460 mcg, more preferably 360-440 mcg, even more preferably 380-420 mcg, most preferably 400 mcg. Folic acid may be substituted by folinic acid or salts thereof, such as e.g. calcium folinate.

In an even more preferred embodiment of the invention, the unit dosage comprises L-arginine, L-citrulline, D-alpha-tocopherol, L-ascorbic acid, alpha-lipoic acid, folic acid and one or more proanthocyanidins, wherein L-arginine or a physiologically acceptable salt or hydrate thereof in the range from 4-10 g, such as 4.4-9.5 g, such as 4.6-9.0 g, such as 4.8-8.0 g, preferably 5.0-7.0 g, more preferably 5.2-6.8 g, even more preferably 5.4-6.6 g, 5.6-6.4 g, 5.8-6.2 g, most preferably 6.0 g, the L-citrulline or a physiologically acceptable salt or hydrate thereof in the range from 0.5-2.0 g, such as 0.7-1.9 g, preferably 0.9-1.8 g, more preferably 1.1-1.7 g, even more preferably 1.3-1.6 g, most preferably 1.5 g, the D-alpha-tocopherol or a physiologically acceptable salt or hydrate thereof in the range from 85-185 mg, such as 90-180 mg, such as 95-175 mg, such as 100-170 mg, such as 105-165 mg, such as 110-160 mg, such as 115-155 mg, preferably 120-150 mg, more preferably 125-145 mg, even more preferably 130-140 mg, most preferably 133 mg, the L-ascorbic acid or a physiologically acceptable salt or hydrate thereof in the range from 300-700 mg, such as 320-680 mg, such as 340-660 mg, such as 360-640 mg, such as 380-620 mg, such as 400-600 mg, such as 420-580 mg, preferably 440-560 mg, more preferably 460-540 mg, even more preferably 480-520 mg, most preferably 500 mg, the alpha-lipoic acid or a physiologically acceptable salt or hydrate thereof is in the range from 5-15 mg, such as 5.5-14.5 mg, such as 6-14 mg, such as 6.5-13.5 mg, such as 7-13 mg, such as 7.5-12.5 mg, such as 8-12 mg, preferably 8.5-11.5 mg, more preferably 9-11 mg, even more preferably 9.5-10.5 mg, most preferably 10 mg, the folic acid or a physiologically acceptable salt or hydrate thereof in the range from 200-600 mcg, such as 220-580 mcg, such as 240-560 mcg, such as 260-540 mcg, such as 280-520 mcg, such as 300-500 mcg, such as 320-480 mcg, preferably 340-460 mcg, more preferably 360-440 mcg, even more preferably 380-420 mcg, most preferably 400 mcg and one or more proanthocyanidins in the range from 10-220 mg, such as 15-210 mg, such as 20-200 mg, such as 25-190 mg, such as 30-180 mg, such as 35-170 mg, such as 40-160 mg, preferably 50-140 mg, more preferably 60-120 mg, even more preferably 70-100 mg, most preferably 80 mg.

In an embodiment of the invention, the unit dosage comprises calcium in the range from 20-100 mg, such as 25-95 mg, such as 30-90 mg, such as 35-85 mg, such as 40-80 mg, preferably 45-75 mg, more preferably 50-70 mg, even more preferably 55-65 mg, most preferably 60 mg.

In an even more preferred embodiment of the invention, the unit dosage comprises L-arginine, L-citrulline, D-alpha-tocopherol, L-ascorbic acid, alpha-lipoic acid, folic acid, calcium and one or more proanthocyanidins, wherein L-arginine or a physiologically acceptable salt or hydrate thereof in the range from 4-10 g, such as 4.4-9.5 g, such as 4.6-9.0 g, such as 4.8-8.0 g, preferably 5.0-7.0 g, more preferably 5.2-6.8 g, even more preferably 5.4-6.6 g, 5.6-6.4 g, 5.8-6.2 g, most preferably 6.0 g, the L-citrulline or a physiologically acceptable salt or hydrate thereof in the range from 0.5-2.0 g, such as 0.7-1.9 g, preferably 0.9-1.8 g, more preferably 1.1-1.7 g, even more preferably 1.3-1.6 g, most preferably 1.5 g, the D-alpha-tocopherol or a physiologically acceptable salt or hydrate thereof in the range from 85-185 mg, such as 90-180 mg, such as 95-175 mg, such as 100-170 mg, such as 105-165 mg, such as 110-160 mg, such as 115-155 mg, preferably 120-150 mg, more preferably 125-145 mg, even more preferably 130-140 mg, most preferably 133 mg, the L-ascorbic acid or a physiologically acceptable salt or hydrate thereof in the range from 300-700 mg, such as 320-680 mg, such as 340-660 mg, such as 360-640 mg, such as 380-620 mg, such as 400-600 mg, such as 420-580 mg, preferably 440-560 mg, more preferably 460-540 mg, even more preferably 480-520 mg, most preferably 500 mg, the alpha-lipoic acid or a physiologically acceptable salt or hydrate thereof is in the range from 5-15 mg, such as 5.5-14.5 mg, such as 6-14 mg, such as 6.5-13.5 mg, such as 7-13 mg, such as 7.5-12.5 mg, such as 8-12 mg, preferably 8.5-11.5 mg, more preferably 9-11 mg, even more preferably 9.5-10.5 mg, most preferably 10 mg, the folic acid or a physiologically acceptable salt or hydrate thereof in the range from 200-600 mcg, such as 220-580 mcg, such as 240-560 mcg, such as 260-540 mcg, such as 280-520 mcg, such as 300-500 mcg, such as 320-480 mcg, preferably 340-460 mcg, more preferably 360-440 mcg, even more preferably 380-420 mcg, most preferably 400 mcg, the calcium in the range from 20-100 mg, such as 25-95 mg, such as 30-90 mg, such as 35-85 mg, such as 40-80 mg, preferably 45-75 mg, more preferably 50-70 mg, even more preferably 55-65 mg, most preferably 60 mg and one or more proanthocyanidins in the range from 10-220 mg, such as 15-210 mg, such as 20-200 mg, such as 25-190 mg, such as 30-180 mg, such as 35-170 mg, such as 40-160 mg, preferably 50-140 mg, more preferably 60-120 mg, even more preferably 70-100 mg, most preferably 80 mg.

In another embodiment, the unit dosage preferably contains caffeine or a physiologically acceptable salt or hydrate thereof in the range from 20-180 mg, such as 30-170 mg, such as 40-160 mg, such as 50-150 mg, such as 60-140 mg, preferably 70-130 mg, more preferably 80-120 mg, even more preferably 90-110 mg, most preferably 100 mg. Alternatively, the compositions may be mixed in caffeine containing soft-drinks prior to use.

In the most preferred embodiment of the invention, the unit dosage comprises L-arginine, L-citrulline, D-alpha-tocopherol, L-ascorbic acid, alpha-lipoic acid, folic acid, calcium, caffeine and one or more proanthocyanidins, wherein L-arginine or a physiologically acceptable salt or hydrate thereof in the range from 4-10 g, such as 4.4-9.5 g, such as 4.6-9.0 g, such as 4.8-8.0 g, preferably 5.0-7.0 g, more preferably 5.2-6.8 g, even more preferably 5.4-6.6 g, 5.6-6.4 g, 5.8-6.2 g, most preferably 6.0 g, the L-citrulline or a physiologically acceptable salt or hydrate thereof in the range from 0.5-3.0 g, such as 0.5-2.9 g, preferably 0.5-2.8 g, more preferably 0.5-2.7 g, such as 0.7-2.0 g, preferably 0.9-2.0 g, more preferably 1.1-2.0 g, even more preferably 1.3-2.0 g, most preferably 1.5-2.0 g, the D-alpha-tocopherol or a physiologically acceptable salt or hydrate thereof in the range from 85-185 mg, such as 90-180 mg, such as 95-175 mg, such as 100-170 mg, such as 105-165 mg, such as 110-160 mg, such as 115-155 mg, preferably 120-150 mg, more preferably 125-145 mg, even more preferably 130-140 mg, most preferably 133 mg, the L-ascorbic acid or a physiologically acceptable salt or hydrate thereof in the range from 300-700 mg, such as 320-680 mg, such as 340-660 mg, such as 360-640 mg, such as 380-620 mg, such as 400-600 mg, such as 420-580 mg, preferably 440-560 mg, more preferably 460-540 mg, even more preferably 480-520 mg, most preferably 500 mg, the alpha-lipoic acid or a physiologically acceptable salt or hydrate thereof is in the range from 5-15 mg, such as 5.5-14.5 mg, such as 6-14 mg, such as 6.5-13.5 mg, such as 7-13 mg, such as 7.5-12.5 mg, such as 8-12 mg, preferably 8.5-11.5 mg, more preferably 9-11 mg, even more preferably 9.5-10.5 mg, most preferably 10 mg, the folic acid or a physiologically acceptable salt or hydrate thereof in the range from 200-600 mcg, such as 220-580 mcg, such as 240-560 mcg, such as 260-540 mcg, such as 280-520 mcg, such as 300-500 mcg, such as 320-480 mcg, preferably 340-460 mcg, more preferably 360-440 mcg, even more preferably 380-420 mcg, most preferably 400 mcg, the calcium in the range from 20-100 mg, such as 25-95 mg, such as 30-90 mg, such as 35-85 mg, such as 40-80 mg, preferably 45-75 mg, more preferably 50-70 mg, even more preferably 55-65 mg, most preferably 60 mg, caffeine or a physiologically acceptable salt or hydrate thereof in the range from 20-180 mg, such as 30-170 mg, such as 40-160 mg, such as 50-150 mg, such as 60-140 mg, preferably 70-130 mg, more preferably 80-120 mg, even more preferably 90-110 mg, most preferably 100 mg and one or more proanthocyanidins in the range from 10-220 mg, such as 15-210 mg, such as 20-200 mg, such as 25-190 mg, such as 30-180 mg, such as 35-170 mg, such as 40-160 mg, preferably 50-140 mg, more preferably 60-120 mg, even more preferably 70-100 mg, most preferably 80 mg.

In another embodiment, the unit dosage preferably contain taurine or a physiologically acceptable salt or hydrate thereof in the range from 200-1800 mg, such as 300-1700 mg, such as 400-1600 mg, such as 500-1500 mg, such as 600-1400 mg, preferably 700-1300 mg, more preferably 800-1200 mg, even more preferably 900-1100 mg, most preferably 1000 mg. Alternatively, the unit dosage may be mixed in caffeine containing soft-drinks prior to use.

In an embodiment of the invention, wherein the unit dosage is a powder composition for dissolution in a soft drink, the powder composition may comprise fewer and/or less amounts of an ingredient already found in the soft drink. In these instances, the soft drink may provide the amount of e.g. caffeine or taurine needed.

The skilled person would understand that the amount of any mentioned ingredient in the unit dosage above may vary depending on the molecular weight of the source of the ingredient (e.g. salt and/or solvate).

Other Optional Ingredients

Besides the active ingredients mentioned above, the compositions may further comprise additional ingredients to improve the organoleptic properties and/or shelf life of the composition such as aromas, natural flavours, acidity regulators and/or preservatives. The skilled person is well aware of suitable aromas, natural flavours, acidity regulators and/or preservatives and the concentrations needed to obtain desired organoleptic properties and improve shelf life.

Thus, in an embodiment of the invention, the composition or unit dosage further comprises one or more aromas. Suitable aromas may include but are not limited to geranyl acetate, methyl acetate, methyl propionate, methyl butyrate, ethyl butyrate, isoamyl acetate, pentyl butyrate, octyl butyrate, pentyl pentanoate, octyl acetate, benzyl acetate, methyl anthranilate, geraniol, nerolidol, limonene, methol, vanillin. Suitable natural flavours may include but are not limited to isoamyl acetate (banana), benzaldehyde (cherry), ethyl propionate, methyl anthranilate (grape), limonene (orange), ethyl decadienoate (pear), ethyl decadienoate (pear), allyl hexanoate (pineapple), ethylvanillin (vanilla), methyl salicylate (wintergreen), manzanate (apple), mango, lemon, lime.

The aqueous solution according to the invention may be adjusted to a desired pH value, in order to obtain a desired balance between organoleptic properties and shelf life of the formulations. The pH may be adjusted by addition of acids or bases (i.e. acidity regulators) until the desired pH is obtained. In principle, any physiologically acceptable base or acid may be used to adjust the pH. Suitable acidity regulators may include but are not limited to carbon dioxide ($CO_2$), hydrogen carbonate ($H_2CO_3$), sulfuric acid ($H_2SO_4$), hydrochloric acid (HCl), acetic acid ($CH_3COOH$), fumaric acid, lactic acid, citric acid, malic acid, glucono delta-lactone, sodium bicarbonate ($NaHCO_3$), potassium acetate, sodium acetate, ammonium acetate ($NH_4CH_3COO$), calcium acetate ($Ca(CH_3COO)_2$), ammonium adipate (($NH_4)_2(C_4H_8(COO)_2)$), calcium gluconate, Epsom salts (magnesium sulfate), sodium aluminium phosphate, sodium hydrogen acetate, sodium succinate, trisodium citrate.

The liquid compositions typically have a pH is in the range of 1 to 7, such as 1.5 to 5.0, preferably 2.0-4.0, more preferably 2.5-3.5. In a preferred embodiment, the acidity regulator is selected from citric acid and/or trisodium citrate. Often, the pH in the liquid formulations is maintained using a buffer solution comprising any of above mentioned pH regulators. Depending on the final pH and buffer capacity desired suitable buffer system may be chosen. Buffers has the usual meaning in the art and have the ability to counteract the addition of both strong acids and bases. The typical preparation of buffers involves dissolving a single compound and adjusting the pH with a strong acid or base. Typical buffers used in the present context include but are not limited to carbonate buffers ($H_2CO_3/HCO_3^-/CO_3^{2-}$), acetic acid/acetate buffers ($CH_3COOH/CH_3COO^-$), citric acid/citrate buffers ($C_3H_5O(COOH)_3/C_3H_5O(COO)^{3-}{}_3$), phosphate buffers ($H_3PO_4/H_2PO_4/HPO_4^{2-}/PO_4^{3-}$) and/or tartaric acid/tartrate buffers ($HOOC(CHOH)_2COOH/HOOC(CHOH)_2COO^-/{}^-OOC(CHOH)_2COO^-$).

Suitable antimicrobial agents may include but are not limited to sorbic acid (E200), sodium sorbate (E201), potassium sorbate (E202), benzoic acid (E210), sodium benzoate (E211), potassium benzoate (E212), calcium benzoate (E213), ethyl 4-hydroxybenzoate (E214), ethyl 4-hydroxybenzoate sodium salt (E215), propyl 4-hydroxybenzoate (E216), propyl 4-hydroxybenzoate sodium salt (E217), methyl 4-hydroxybenzoate (E218), methyl 4-hydroxybenzoate sodium salt (E219), sulphur dioxide (E220), sodium sulphite (E221), sodium hydrogen sulphite (E222), sodium metabisulphite (E223), potassium metabisulphite (E224), potassium sulphite (E225), calcium sulphite (E226), calcium hydrogen sulphite (E227), potassium nitrite (E249), sodium nitrite (E250), sodium nitrate (E251), potassium nitrate (E252), lactic acid (E270), propionic acid (E280), sodium propionate (E281)m calcium propionate (E282), potassium propionate (E283) or mixtures thereof. In a preferred embodiment, the antimicrobial agent is potassium sorbate (E202) and/or sodium benzoate (E211).

Suitable antioxidants may include but are not limited to ascorbic acid (E300), sodium ascorbate (E301), calcium ascorbate (E302), ascorbyl palmitate (E304(i)), ascorbyl stearate (E304(ii)), propyl gallate (E310), octyl gallate (E311), dodecyl gallate (E312), butylated hydroxyanisole (E320), butylated hydroxytoluene (E321) or mixtures thereof. In a preferred embodiment, the antioxidant is calcium ascorbate (E302). The compositions according to the invention may further comprise one or more ingredients selected from the group consisting of taurine, caffeine, calcium, or an acceptable salt or hydrate of anyone thereof. In the most preferred embodiment of the invention, the unit dosage is a powder composition that is dissolved in a commercial beverage, such that no additional ingredients besides the active ingredients are needed in the unit dosage.

A wide range of physiologically acceptable salts are well-known to the skilled person in the art. The invention intends to include any physiologically acceptable salt. As mere non-limiting examples, cations typically found in acceptable salts are selected from an alkali metal or alkaline earth metal ions or combinations thereof. Thus, suitable salts of acids may be formed by treating an acid with a suitable base (e.g. NaOH). These salts may include a lithium ($Li^+$) salt, sodium ($Na^+$) salt, potassium ($K^+$) salt, magnesium ($Mg^{2+}$) salt or a calcium ($Ca^{2+}$) salt of the acid or any combinations thereof. Furthermore, suitable salts of bases may be formed by treating a base with an appropriate acid (e.g. HCl). These salts may include a chloride ($Cl^-$) salt, a bromide ($Br^-$) salt, an iodide ($I^-$) salt, an acetate ($CH_3COO^-$) salt, a tosylate ($CH_3C_6H_4SO_2^-$) salt, a tartrate ($C_4H_5O_6^-/C_4H_4O_6^{2-}$) salt, a sulfate ($HSO_4^-/SO_4^{2-}$) salt, a succinate ($(CH_2)_2(COO)_2^{2-}$) salt, a phosphate ($H_2PO_4^-/HPO_4^{2-}/PO_4^{3-}$) salt, a nitrate ($NO_3^-$) salt, a mesylate ($CH_3SO_3^-$) salt, a maleate ($^-O_2CCH=CHCOO^-/HO_2CCH=CHCOO^-$) salt, a malate salt, a citrate salt of the base or any combinations thereof.

Use of the Compositions

As described above, the inventors surprisingly found that compositions according to the present invention could be used by healthy human subjects as single dosage compositions (at relatively low dosages) avoiding the drawbacks of continuous treatment while providing the benefits of achieving improved sexuality on demand.

Thus, in a particularly preferred embodiment, the present invention relates to a composition or unit dosage according to the first aspect above for use in improving the sexual function of a sexually healthy human subject. In particular, the compositions are intended for use for administration on demand (non-continuous). Further, the compositions are intended for use in improving the sexual function of a sexually healthy female. Further, the compositions are intended for use in improving the sexual function of a sexually healthy male. Even further, the compositions are intended for use for improving sexual function of sexually healthy subjects of both sexes simultaneously.

The inventors found that the composition according to the invention improved the sexual function in sexually normally functioning heterosexual men and women as well as in sexually normally functioning homosexual women.

In the examples below, the following parameters were tested:
a. Sexual arousal score (male and female),
b. emotional satisfaction (male and female),
c. intercourse in general score (male and female),
d. erection hardness (males only)
e. de-sensitivity to penis score (male),
f. IELT score (male),
g. lubrication score (female),
h. orgasm score (female),
i. discomfort during penetration score (female) (only example 1).

Sexual Arousal

This score is a measure of the sexual desire before and during sexual activity. Sexual arousal is a feeling that includes both physical and mental aspects of sexual excitement. It may include feelings of warmth or tingling in the genitals, lubrication (wetness), or muscle contractions. A number of physiological responses occur in the body and mind as preparation for sexual intercourse and continue during it. Male arousal will lead to an erection, and in female arousal the body's response is engorged sexual tissues such as nipples, vulva, clitoris, vaginal walls and vaginal lubrication. Mental stimuli and physical stimuli such as touch, and the internal fluctuation of hormones, can influence sexual arousal. In example 1, sexual arousal was evaluated on a 1-5 scale where 1 is "Very low", 2 is "low", 3 is "moderate", 4 is "high" and 5 is "Very high".

In example 2, the score was evaluated as follows: 0—None, 1—Very low, 2—Normal, 3—Moderately higher than normal, 4—High, 5—Very high.

Emotional Satisfaction

This score is a measure of the level of emotional intimacy between partners during and after sexual activity. Emotional satisfaction is an essential part of relationships and the experience of sexual health and functioning. In example 1, emotional satisfaction was evaluated on a 1-5 scale where 1 is "moderately dissatisfied", 2 is "Equally satisfied and dissatisfied", 3 is "Moderately satisfied", 4 is "Very satisfied" and 5 is "extremely satisfied".

In example 2, the score was evaluated as follows: 0—very dissatisfied, 1—dissatisfied, 2—Normal, 3—More satisfied than normal, 4—very satisfied, 5—Extremely satisfied.

Intercourse in General Score

This score is a measure of the general overall assessment of a single sexual experience. In example 1, intercourse in general was evaluated on a 1-5 scale where 1 is "Moderately dissatisfied", 2 is "Equally satisfied and dissatisfied", 3 is "Moderately satisfied", 4 is "Very satisfied" and 5 is "Extremely satisfied".

In example 2, the score was evaluated as follows: 0—very dissatisfied, 1—dissatisfied, 2—Normal, 3—More satisfied than normal, 4—very satisfied, 5—Extremely satisfied.

Erection Hardness (EHS) (Males Only)

In example 1, his score is a measure of the general hardness of penis prior to penetration. Erection hardness was evaluated on a 1-5 scale where 1 is "penis was larger, but not hard", 2 is "Penis was hard, but not hard enough for penetration", 3 is "penis was hard enough for penetration, but not completely hard", 4 is "Penis was very hard and rigid" and 5 is "Penis was completely hard and fully rigid".

In example 2, the score was evaluated as follows: 0—Penis did not enlarge, 1—Penis was larger, but not hard, 2—Penis was hard as normal, 3—Penis was harder than normal, 4—Penis was much harder than normal, 5—Penis was much harder than normal and for much longer period of time.

De-Sensitivity to Penis Score (Males Only)

This score is a measure of the sensitivity of the penis during sexual activity. In example 1, de-sensitivity was evaluated on a 1-5 scale where 1 is "penis head skin was slightly more sensitive", 2 is "penis head skin had normal sensitivity", 3 is "penis head skin had slightly less sensitivity", 4 is "penis head skin had a moderate desensitivity" and 5 is "penis head skin had a clear desensitivity". In example 2, the score was evaluated as follows: 0—Penis head skin was very sensitive, 1—Penis head skin was slightly more sensitive, 2—Penis head skin had normal sensitivity, 3—Penis head skin had slightly less sensitivity, 4—Penis head skin had a clear desensitivity, 5—Penis head skin had a pronounced desensitivity.

IELT Score (Males Only)

Intravaginal ejaculation latency time (IELT) is the time taken by a man to ejaculate during vaginal penetration. IELT is known to vary, not only from man to man, but also from one time to the next for the same man and tends to decrease with age. Studies have shown that median IELT decreased with age (ages 18-30: 6.5 minutes, ages 31-50: 5.4 minutes, aged above 51: 4.3 minutes).

Male participants in examples 1 and 2 recorded the IELT during the studies.

Lubrication Score (Females Only)

This score assesses how difficult/easy it was to become lubricated ("wet") during sexual activity or intercourse. In example 1, lubrication was evaluated on a 1-5 scale where 1 is "Very difficult", 2 is "Difficult", 3 is "Normal", 4 is "Easy" and 5 is "Very easy".

In example 2, the score was evaluated as follows: 0—Extremely difficult or impossible, 1—Very difficult, 2—Normal, 3—Easier than normal, 4—Very easy, 5—Very easy (really "wet").

Orgasm score (females only) This score assesses the level of female orgasm (climax) during the sexual activity. In example 1, orgasm score was evaluated on a 1-5 scale where 1 is "difficult to reach orgasm", 2 is "normal", 3 is "Easy to reach orgasm", 4 is "Very easy to reach orgasm" and 5 is "multiple orgasms".

In example 2, the score was evaluated as follows: 0—No orgasm, 1—Difficult to reach orgasm, 2—Normal, 3—Easy to reach orgasm, 4—Very easy to reach orgasm, 5—Multiple orgasms.

Discomfort During Penetration Score (Females Only, Example 1 Only)

This score assesses the level of female discomfort or pain during or following vaginal penetration. In example 1, discomfort was evaluated on a 1-5 scale where 1 is "high", 2 is "moderate", 3 is "low", 4 is "very low" and 5 is "none".

As seen in the examples, the compositions were tested on heterosexual couples and homosexual female couples. Notably, the compositions showed very significant effect in homosexual women, thereby documenting surprising effects on females (without any involvement of a male subject). Thus, in an embodiment of the invention, the human subject is a female. In another embodiment of the invention, the human subject is a heterosexual woman. In yet another embodiment, the human subject is a homosexual woman.

Sexual function typically declines with age due to hormonal changes. Thus, in yet another embodiment, the compositions are for use in improving sexual function in a postmenopausal woman. In an embodiment of the invention, the human subject is a heterosexual man. Even not tested, one may expect the same beneficial effects of the compositions in homosexual men. Thus, in yet another embodiment the human subject is a homosexual man. The composition was effective in heterosexual couples (i.e. both men and women) when administered in the same dose amount (i.e. a unit dosage). Thus, another advantage of the invention is a unit dosage that fits both men and women.

Without being bound to theory, the composition may in part work by improving NO production in situ. Thus, in an embodiment of the invention, the composition or unit dosage according to the first aspect may be used in improving genital blood flow.

The unit dosage of the invention is intended to be used as a one dose fits all. However, the unit dosage is designed to fit to a sexually healthy subject with a weight of 50-75 kg. In order to obtain maximal effect in sexually dysfunctional subjects, as well as subjects having higher weights, the dosages would most probably have to be increased.

However, in certain cases, more than a single unit dose may be needed to achieve a desired response. Thus, in an embodiment of the invention, one or more unit doses is administered, as needed prior to sexual activity. Alternatively, one or more unit doses may be used concomitant with other known treatments for sexual disorders or dysfunctions. Thus, the composition or unit dose may be combined with one or more other active ingredients. In an embodiment of the invention, the further active pharmaceutical ingredient is selected from a group consisting of PDE5 inhibitors, androgens, estrogens and/or progesterons.

The inventors found that the unit dose needs to be administered at a certain time period prior to sexual activity to obtain the best clinical outcome. Significantly, the unit dosage compositions according to the invention were found to provide effect already 30 minutes after consumption, and it was found that maximal effect was obtain already after 1-1.5 hours. The effect was observed to decline slowly thereafter until 24 after consumption. Thus, in an embodiment, the composition or unit dosage is consumed 0.5-12.0 hours prior to sexual activity, such 0.5-5.5 hours prior to sexual activity, such as 1.0-5 hours, preferably 1.0-4.5 hours, more preferably 1.0-4.0 hours, most preferably 1.0-3.5 hours, such as 1.0-3.0 hours prior to sexual activity.

Medical Use

A second aspect of the present invention relates to a composition or unit dosage according to the first aspect for use as a medicament.

As the skilled person would appreciate, in order to obtain maximal effect in sexually dysfunctional subjects, the dosages would most probably have to be increased. Significant increases in dosage (>2 times the on-demand dosages described above) may be accompanied with side-effect (mostly stomach problems) having a negative effect on the sexual functioning of the subject as well as the sexual partner of the subject. However, adhering to the dosage regimens described herein will provide significant benefits also to sexually dysfunctional subjects.

Thus, more particularly, the second aspect relates to a pharmaceutical composition or unit dosage according to the first aspect, for use in the treatment of a sexually related disorder or dysfunction in a human subject.

In a preferred embodiment of the invention, the sexual related disease, disorder or dysfunction is selected from endothelial dysfunction, erectile dysfunction, sexual arousal disorder, hypoactive sexual desire disorder (HSDD), sexual aversion disorder (SAD), orgasmic disorder (anorgasmia), premature ejaculation, dyspareunia, vaginismus and/or sexual dissatisfaction (non-specific).

Aspects of the Invention

1. A composition comprising L-arginine and L-citrulline or a physiologically acceptable salt or hydrate of any one thereof, wherein the molar ratio of L-arginine:L-citrulline is in the range from 2.2:1 to 10.0:1, preferably from 2.2:1 to 5.8:1, even more preferably from 3:1 to 5:1.

2. A composition according to the above aspect 1, wherein the composition comprises one or more proanthocyanidins.

3. A composition according to anyone of the above aspects, wherein the composition is in a unit dosage form and wherein the content of L-arginine or a physiologically acceptable salt or hydrate thereof is at least 4.0 g, such as in the range of from 4.0-10.0 g, preferably 4.0-8.0 g.

4. A composition according to any of the above aspects 1-3, wherein the content of L-arginine or a physiologically acceptable salt or hydrate thereof is at least 4.0 g, such as in the range from 4.0-10.0 g and the content of L-citrulline or a physiologically acceptable salt or hydrate thereof is at least 1.0 g, such as preferably in the range from 1.0-3.0 g.

5. A composition or unit dosage according to anyone of the above aspects for use in improving the sexual function in a sexually healthy human subject.

6. A composition or unit dosage for use according to the above aspect 5 for use in improving sexual arousal in a sexually healthy human subject.

7. A composition or unit dosage for use according to any one of the above aspects 5 or 6, wherein the human subject is a female.

8. A composition or unit dosage for use according to the above aspect 7, for use in improving orgasmic function in a sexually healthy female subject.

9. A composition or unit dosage for use according to any one of the above aspects 5 or 6, wherein the human subject is a male.

10. A composition or unit dosage for use according to the above aspect 9, for use in improving IELT in a sexually healthy male subject.

11. A unit dosage for use according to any of the above aspects 5-10, wherein one or more unit doses is administered 0.5-5.5 hours prior to sexual activity, such as 1.0-5 hours, preferably 1.0-4.5 hours, more preferably 1.0-4.0 hours, most preferably 1.0-3.5 hours, such as 1.0-3.0 hours prior to sexual activity.

12. Use of a pharmaceutical composition or unit dosage according to anyone of the above aspects 1-4 for improving sexuality and/or sexual function of a healthy human subject for a time period of up to 6 hours.

13. A method of improving sexuality and/or sexual function of a healthy human subject for a time period of up to 6 hours comprising the steps of administering one or more unit dosages according to any one of the above aspects 1-4 to the subject.

14. A pharmaceutical composition or unit dosage according to anyone of the above aspects 1-4 for use as a medicament.

15. A pharmaceutical composition or unit dosage according to anyone of the above aspects, for use in the treatment of a sexual disorder or dysfunction in a human subject, wherein the sexual disorder or dysfunction is selected from the group consisting of endothelial dysfunction, erectile dysfunction, impotence, sexual arousal disorder, hypoactive sexual desire disorder (HSDD), sexual aversion disorder (SAD), orgasmic disorder (anorgasmia), premature ejaculation, dyspareunia, vaginismus and/or sexual dissatisfaction (non-specific).

The following figures and examples are provided below to illustrate the present invention. They are intended to be illustrative and are not to be construed as limiting in any way.

EXAMPLES

General:
Clinical Trial Setup

In example 1 below a double blinded placebo-controlled clinical trial was conducted with a composition according to the invention. Two treatment groups were generated consisting of 10 heterosexual couples and 10 homosexual couples (females). Each couple in each treatment group received six sets of bottles (labeled A-F) containing either the active powder mixture (3 sets of bottles) or the placebo mixture (3 sets of bottles) and instructions for producing the test drink. The colour, taste and smell of the test drinks and placebo drinks were nearly identical. The couples were asked to pick two bottles with the same label for consumption prior to sexual activity and rate the intercourse afterwards.

The treatment bottles contained 12 grams powder mixture comprising 500 mg Vitamin C (as Calcium Ascorbate Acid), 200 IU Vitamin E (as D-Alpha Tocopheryl Acetate), 400 µg Folic Acid, 60 mg Calcium, 10 mg Alpha Lipoic acid, 6 g L-Arginine, 1.5 g L-Citrulline, 1000 mg L-taurin, 100 mg Caffeine and 80 mg Pycnogenol®, the remainder of the composition being sugar.

The placebo bottles contained 12 grams powder mixture comprising 500 mg Vitamin C (as Calcium Ascorbate Acid), 200 IU Vitamin E (as D-Alpha Tocopheryl Acetate), 400 µg Folic Acid, 60 mg Calcium, 10 mg Alpha Lipoic acid, 0.5 g L-Arginine, 1000 mg L-taurin, and 100 mg Caffeine, the remainder of the composition being sugar.

Visual appearance of test and placebo mixtures was identical. L-arginine is characterized by an undesired taste and smell. Due to the presence of a small amount of L-Arginine in the placebo composition, the taste and smell of test and placebo mixtures were (nearly) identical and indistinguishable after mix with a relevant soft drink.

In example 2 below a double blinded clinical trial was conducted with a composition according to the invention and reference compositions comprising varying amounts of the active ingredients. Three treatment groups were generated consisting of 2 heterosexual couples and 2 homosexual couples (females). Each couple in each treatment group tested 3 different compositions. All couples received six sets of bottles containing either the active powder mixture (2 sets of bottles labelled A, received by all couples) or a reference/treatment mixture (each couple received 2*2 sets of reference/treatment mixture bottles labeled B-G, respectively) and instructions for producing the test drink. The colour, taste and smell of the test drinks and reference drinks were identical. The couples were asked to pick two bottles with the same label for consumption prior to sexual activity and rate the intercourse afterwards.

The treatment bottles labelled "A" contained 6 g L-arginine, 1.5 g L-citrulline and 80 mg Pycnogenol® as well as an additive mixture comprising: 500 mg Vitamin C (as Calcium Ascorbate Acid), 200 IU Vitamin E (as D-Alpha Tocopheryl Acetate), 400 µg Folic Acid, 60 mg Calcium, 10 mg Alpha Lipoic acid, 1000 mg L-taurin and 100 mg Caffeine.

The reference bottles labelled "B" contained 6 g L-arginine, 1.5 g L-citrulline as well as an additive mixture comprising: 500 mg Vitamin C (as Calcium Ascorbate Acid), 200 IU Vitamin E (as D-Alpha Tocopheryl Acetate), 400 µg Folic Acid, 60 mg Calcium, 10 mg Alpha Lipoic acid, 1000 mg L-taurin and 100 mg Caffeine. These compositions lacked the source of proanthocyanidins; Pycnogenol® compared to the bottles A.

The reference bottles labelled "C" contained 6 g L-arginine and 80 mg Pycnogenol® as well as an additive mixture comprising: 500 mg Vitamin C (as Calcium Ascorbate Acid), 200 IU Vitamin E (as D-Alpha Tocopheryl Acetate), 400 µg Folic Acid, 60 mg Calcium, 10 mg Alpha Lipoic acid, 1000 mg L-taurin and 100 mg Caffeine. These compositions lacked citrulline compared to the bottles A.

The treatment (compositions according to the invention) bottles labelled "D" contained 6 g L-arginine, 2.0 g L-citrulline and 80 mg Pycnogenol® as well as an additive mixture comprising: 500 mg Vitamin C (as Calcium Ascorbate Acid), 200 IU Vitamin E (as D-Alpha Tocopheryl Acetate), 400 µg Folic Acid, 60 mg Calcium, 10 mg Alpha Lipoic acid, 1000 mg L-taurin and 100 mg Caffeine. These compositions had a slightly increased amount of citrulline compared to the bottles A.

The reference bottles labelled "E" contained 7.5 g L-citrulline and 80 mg Pycnogenol® as well as an additive mixture comprising: 500 mg Vitamin C (as Calcium Ascorbate Acid), 200 IU Vitamin E (as D-Alpha Tocopheryl Acetate), 400 µg Folic Acid, 60 mg Calcium, 10 mg Alpha Lipoic acid, 1000 mg L-taurin and 100 mg Caffeine. These compositions had a total amount of citrulline that was identical to the total amount of arginine+citrulline in the bottles A.

The reference bottles labelled "F" contained 3 g L-arginine, 1.5 g L-citrulline and 80 mg Pycnogenol® as well as an additive mixture comprising: 500 mg Vitamin C (as Calcium Ascorbate Acid), 200 IU Vitamin E (as D-Alpha Tocopheryl Acetate), 400 microgram (mcg) Folic Acid, 60 mg Calcium, 10 mg Alpha Lipoic acid, 1000 mg L-taurin and 100 mg Caffeine. These compositions had a decreased amount of arginine compared to the bottles A.

The reference bottles labelled "G" contained 3 g L-arginine, 3.5 g L-citrulline and 80 mg Pycnogenol® as well as an additive mixture comprising: 500 mg Vitamin C (as Calcium Ascorbate Acid), 200 IU Vitamin E (as D-Alpha Tocopheryl Acetate), 400 microgram (mcg) Folic Acid, 60 mg Calcium, 10 mg Alpha Lipoic acid, 1000 mg L-taurin and 100 mg Caffeine. These compositions had a decreased amount of arginine. These compositions had a decreased amount of arginine and an increased amount of citrulline. The total amount of citrulline+arginine that was identical to the total amount of arginine+citrulline in the bottles A with different arginine:citrulline ratio.

The colour, taste and smell of the bottles A-G were nearly identical.

The homosexual and heterosexual females were asked to rate their sexual arousal score, lubrication score, orgasm score, emotional satisfaction score and intercourse in general score from 1-5 (example 1) or 0-5 (example 2).

The heterosexual males were asked to rate their sexual arousal score, emotional satisfaction score, intercourse in general, erection hardness score, de-sensitivity to penis score from 1-5 (example 1) or 0-5 (example 2) and to measure their IELT score.

The study was supervised by a physician (investigator), who was not informed of the identity of the set of bottles or the contents of the test mixtures. The test was performed under confidentiality both for the participants and the investigator.

Couples were given the below instructions.

Instructions:

1) Plan a Test/Intercourse Event.

Plan an intercourse event. Only start the test procedure in case you have a reasonable expectation that other conditions for sexual arousal are favourable.

Pick 2 bottles with the same label. You are free to choose any label.

2) Production of Test Drink:

Just prior to consumption, add the soft drink (lemon soda) to the test bottles (approx. 250 ml) and mix the dry powder by gently shaking the test bottle until all the dry power is dissolved (it may take several minutes. It is important that the material is completely dissolved in the tester) to generate the drink tester. Please note that the label of the bottle and the time and date of the consumption of the drink tester in the accompanying questionnaire.

3) Consumption of Test Drink

Consume one tester drink per subject, at least 1 hour prior to—preferably 2-3 hours prior to—and no more than 5 hours prior to the planned intercourse event. Please consume the tester drink at least one hour before a low-fat meal, or alternatively, at least two hours after a low-fat meal.

4) Intercourse

Perform an intercourse event at least 1 hour after—preferably 2-3 hours after—and no more than 5 hours after consumption of test drink.

5) Questionnaire

Following intercourse (preferably immediately after intercourse), please answer the questionnaire by filling in the accompanying data sheet.

6) Repeat Procedure

Repeat the above procedure 6 times (until all bottles are consumed). Each intercourse event should be separated by at least two days without sexual activity. Please answer the questionnaire after each event of intercourse event.

All test subjects defined their sexual functioning as being normal (no sexual dysfunctions) prior to the study.

Example 1a—Results of Heterosexual Males

In example 1 a paired t-test was used to compare the mean scores of the treatment arms (heterosexual men, heterosexual woman or homosexual woman) with the placebo arms (heterosexual men, heterosexual woman or homosexual woman).

Paired t-test: Is there a difference between the placebo arm and treatment arm in the different scores?

Null hypothesis $\mu_D=0$

Alternative hypothesis $\mu_D>0$

Level of significance $\alpha=0.05$, t=1,833 at $\alpha=0.05$ and degree of freedom=9

Level of significance $a = 0.05$, $t = 1,833$ at $a = 0.05$ and degree of freedom = 9

$$t = \frac{\overline{D}}{s_D/\sqrt{n}}$$

where D and g is given by:

$$\overline{D} = \frac{\sum_i^n D_i}{n}, \quad S_D^2 = \frac{\sum_i^n (D_i - \overline{D})^2}{n-1}$$

Sexual Arousal Score

CONCLUSION

The results show a mean improvement of 1.43 points (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (MJ) | 3.00 | 5.00 | 2.00 |
| 2 (DL) | 3.00 | 5.00 | 2.00 |
| 3 (JR) | 3.00 | 3.00 | 0.00 |
| 4 (AM) | 3.67 | 5.00 | 1.33 |
| 5 (TM) | 3.00 | 5.00 | 2.00 |
| 6 (MS) | 2.67 | 5.00 | 2.33 |
| 7 (NE) | 3.67 | 5.00 | 1.33 |
| 8 (RH) | 3.00 | 3.00 | 0.00 |
| 9 (TR) | 3.67 | 5.00 | 1.33 |
| 10 (MW) | 3.00 | 5.00 | 2.00 |
| SUM (X − Y) | | | 14.3 |
| $\overline{D}$ (mean difference) | | | 1.43 |
| $S_D$ | | | 1.14 |
| t-value | | | 2.98 |
| t-value > 1.833 | | | Significant difference |

Emotional Satisfaction Score

Conclusion:

There is a mean improvement of 1.00 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (MJ) | 3.00 | 4.00 | 1.00 |
| 2 (DL) | 3.00 | 4.00 | 1.00 |
| 3 (JR) | 2.00 | 3.00 | 1.00 |
| 4 (AM) | 3.33 | 4.00 | 0.67 |
| 5 (TM) | 2.67 | 4.00 | 1.33 |
| 6 (MS) | 2.33 | 4.00 | 1.67 |
| 7 (NE) | 3.00 | 4.00 | 1.00 |
| 8 (RH) | 2.67 | 3.00 | 0.33 |
| 9 (TR) | 3.00 | 4.00 | 1.00 |
| 10 (MW) | 3.00 | 4.00 | 1.00 |
| SUM (X − Y) | | | 10.0 |
| $\overline{D}$ (mean difference) | | | 1.00 |
| $S_D$ | | | 0.60 |
| t-value | | | 5.37 |
| t-value > 1.833 | | | Significant difference |

Intercourse in General Score

Conclusion:

The results show a mean improvement of 1.00 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (MJ) | 3.00 | 4.00 | 1.00 |
| 2 (DL) | 3.00 | 4.00 | 1.00 |
| 3 (JR) | 2.00 | 3.00 | 1.00 |
| 4 (AM) | 3.33 | 4.00 | 0.67 |
| 5 (TM) | 2.67 | 4.00 | 1.33 |
| 6 (MS) | 2.33 | 4.00 | 1.67 |
| 7 (NE) | 3.00 | 4.00 | 1.00 |
| 8 (RH) | 2.67 | 3.00 | 0.33 |
| 9 (TR) | 3.00 | 4.00 | 1.00 |
| 10 (MW) | 3.00 | 4.00 | 1.00 |
| | SUM (X − Y) | | 10.0 |
| | $\overline{D}$ (mean difference) | | 1.00 |
| | $S_D$ | | 0.59 |
| | t-value | | 5.37 |
| | t-value > 1.833 | | Significant difference |

Erection Hardness Score

Conclusion:

The results show a mean improvement of 0.73 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (MJ) | 3.00 | 4.00 | 1.00 |
| 2 (DL) | 3.00 | 4.00 | 1.00 |
| 3 (JR) | 3.00 | 3.00 | 0.00 |
| 4 (AM) | 3.33 | 4.00 | 0.67 |
| 5 (TM) | 3.00 | 4.00 | 1.00 |
| 6 (MS) | 3.00 | 4.00 | 1.00 |
| 7 (NE) | 3.33 | 4.00 | 0.67 |
| 8 (RH) | 3.00 | 3.00 | 0.00 |
| 9 (TR) | 3.33 | 4.00 | 0.67 |
| 10 (MW) | 3.00 | 4.33 | 0.67 |
| | SUM (X − Y) | | 7.34 |
| | $\overline{D}$ (mean difference) | | 0.73 |
| | $S_D$ | | 0.63 |
| | t-value | | 3.37 |
| | t-value > 1.833 | | Significant difference |

De-Sensitivity to Penis Score

Conclusion:

The results show a mean improvement of 1.83 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (MJ) | 2.00 | 4.00 | 2.00 |
| 2 (DL) | 1.67 | 4.00 | 2.33 |
| 3 (JR) | 1.00 | 1.00 | 0.00 |
| 4 (AM) | 2.00 | 4.00 | 2.00 |
| 5 (TM) | 1.67 | 4.00 | 2.33 |
| 6 (MS) | 1.00 | 4.00 | 3.00 |
| 7 (NE) | 2.33 | 4.00 | 1.67 |
| 8 (RH) | 1.33 | 2.00 | 0.67 |
| 9 (TR) | 2.67 | 4.00 | 1.33 |
| 10 (MW) | 1.00 | 4.00 | 3.00 |
| | SUM (X − Y) | | 18.3 |
| | $\overline{D}$ (mean difference) | | 1.83 |
| | $S_D$ | | 1.39 |
| | t-value | | 4.16 |
| | t-value > 1.833 | | Significant difference |

IELT Score

IELT is known to vary, not only from man to man, but from one time to the next for the same man and tends to decrease with age. Studies have shown that median IELT decreased with age (18-30: 6.5 minutes, 31-50: 5.4 minutes, above 51: 4.3 minutes). Median IELT for all participants was 5.4 minutes. Some medications such as selective serotonin reuptake inhibitors (SSRIs) affect IELT.

Conclusion:

The test composition provides a mean improvement of 236.8 seconds, which is statistically significant (P<0.05).

Detailed Results:

| Individual | Placebo (sec) (Y) Mean of 3 tests | Treatment (sec) (X) Mean of 3 tests | X − Y |
|---|---|---|---|
| 1 (MJ) | 387 | 784 | 397 |
| 2 (DL) | 373 | 775 | 402 |
| 3 (JR) | 367 | 361 | −6 |
| 4 (AM) | 484 | 728 | 244 |
| 5 (TM) | 345 | 680 | 335 |
| 6 (MS) | 339 | 686 | 347 |
| 7 (NE) | 447 | 693 | 246 |
| 8 (RH) | 289 | 299 | 10 |
| 9 (TR) | 381 | 579 | 198 |
| 10 (MW) | 386 | 581 | 195 |
| | SUM (X − Y) | | 2368 |
| | $\overline{D}$ (mean difference) | | 236.8 |
| | $S_D$ | | 170.8 |
| | t-value | | 4.38 |
| | t-value > 1.833 | | Significant difference |

Example 1b—Results of Heterosexual Females

Sexual Arousal Score

Sexual arousal (also sexual excitement) is the arousal of sexual desire, during or in anticipation of sexual activity. A number of physiological responses occur in the body and mind as preparation for sexual intercourse and continue during it. Male arousal will lead to an erection, and in female arousal, the body's response is engorged sexual tissues such as nipples, vulva, clitoris, vaginal walls and vaginal lubrication. Mental stimuli and physical stimuli such as touch, and the internal fluctuation of hormones, can influence sexual arousal.

Sexual arousal has several stages and may not lead to any actual sexual activity beyond a mental arousal and the physiological changes that accompany it. Given sufficient sexual stimulation, sexual arousal in humans reaches its climax during an orgasm. It may also be pursued for its own sake, even in the absence of an orgasm.

Conclusion:

The results show a mean improvement of 1.3 point (on a 1-5 scale), which is statistically significant (P<0.05). 2 females (LR and HN) (=80%) are seen as being non-responders. KA is defined as a medium responder.

Detailed Results:

| Individual | Placebo score (Y) Mean of 3 tests | Treatment score (X) Mean of 3 tests | X − Y |
|---|---|---|---|
| 1 (LP) | 3.00 | 5.00 | 2.00 |
| 2 (IM) | 3.67 | 5.00 | 1.33 |
| 3 (SR) | 3.00 | 5.00 | 2.00 |
| 4 (BL) | 3.33 | 5.00 | 1.67 |
| 5 (DS) | 3.33 | 5.00 | 1.67 |
| 6 (KA) | 2.00 | 2.67 | 0.67 |
| 7 (MR) | 2.67 | 5.00 | 2.33 |
| 8 (TC) | 3.67 | 5.00 | 1.33 |
| 9 (LR) | 3.00 | 3.00 | 0.00 |
| 10 (HN) | 1.00 | 1.00 | 0.00 |
| SUM (X − Y) | | | 13.0 |
| $\bar{D}$ (mean difference) | | | 1.30 |
| $S_D$ | | | 0.55 |
| t-value | | | 7.48 |
| t-value > 1.833 | | | Significant difference |

Lubrication Score

Conclusion:

The results show a mean improvement of 1.3 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (LP) | 3.00 | 5.00 | 2.00 |
| 2 (IM) | 3.67 | 5.00 | 1.33 |
| 3 (SR) | 3.00 | 5.00 | 2.00 |
| 4 (BL) | 3.33 | 5.00 | 1.67 |
| 5 (DS) | 3.33 | 5.00 | 1.67 |
| 6 (KA) | 2.33 | 3.00 | 0.67 |
| 7 (MR) | 2.67 | 5.00 | 2.33 |
| 8 (TC) | 3.67 | 5.00 | 1.33 |
| 9 (LR) | 2.33 | 3.00 | 0.67 |
| 10 (HN) | 1.00 | 1.00 | 0.00 |
| SUM (X − Y) | | | 13.7 |
| $\bar{D}$ (mean difference) | | | 1.37 |
| $S_D$ | | | 0.56 |
| t-value | | | 7.68 |
| t-value > 1.833 | | | Significant difference |

Orgasm Score

Conclusion:

Results show a mean improvement of 1.6 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (LP) | 2.00 | 4.67 | 2.67 |
| 2 (IM) | 2.67 | 5.00 | 2.33 |
| 3 (SR) | 2.00 | 4.00 | 2.00 |
| 4 (BL) | 2.67 | 5.00 | 2.33 |
| 5 (DS) | 2.00 | 4.00 | 2.00 |
| 6 (KA) | 1.33 | 2.00 | 0.67 |
| 7 (MR) | 1.67 | 4.00 | 2.33 |
| 8 (TC) | 2.67 | 4.00 | 1.33 |
| 9 (LR) | 1.33 | 2.00 | 0.67 |
| 10 (HN) | 1.00 | 1.00 | 0.00 |
| SUM (X − Y) | | | 16.3 |
| $\bar{D}$ (mean difference) | | | 1.63 |
| $S_D$ | | | 0.69 |
| t-value | | | 7.50 |
| t-value > 1.833 | | | Significant difference |

Emotional Satisfaction Score

Conclusion:

The results show a mean improvement of 0.9 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (LP) | 3.00 | 4.00 | 1.00 |
| 2 (IM) | 3.33 | 4.00 | 0.67 |
| 3 (SR) | 3.00 | 4.00 | 1.00 |
| 4 (BL) | 3.00 | 4.00 | 1.00 |
| 5 (DS) | 2.67 | 4.00 | 1.33 |
| 6 (KA) | 2.33 | 3.00 | 0.67 |
| 7 (MR) | 2.67 | 4.00 | 1.33 |
| 8 (TC) | 3.00 | 4.00 | 1.00 |
| 9 (LR) | 2.33 | 3.00 | 0.67 |
| 10 (HN) | 1.00 | 2.00 | 1.00 |
| SUM (X − Y) | | | 9.67 |
| $\bar{D}$ (mean difference) | | | 0.97 |
| $S_D$ | | | 0.46 |
| t-value | | | 6.67 |
| t-value > 1.833 | | | Significant difference |

Discomfort During Penetration Score

Conclusion:

The results show a mean improvement of 0.9 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (LP) | 4.00 | 5.00 | 1.00 |
| 2 (IM) | 4.33 | 5.00 | 0.67 |
| 3 (SR) | 4.00 | 5.00 | 1.00 |
| 4 (BL) | 3.67 | 5.00 | 1.33 |
| 5 (DS) | 3.67 | 5.00 | 1.33 |
| 6 (KA) | 3.33 | 4.00 | 0.67 |
| 7 (MR) | 3.67 | 5.00 | 1.33 |
| 8 (TC) | 4.00 | 5.00 | 1.00 |
| 9 (LR) | 3.00 | 4.00 | 1.00 |
| 10 (HN) | 2.00 | 2.00 | 0.00 |
| SUM (X − Y) | | | 9.33 |
| $\bar{D}$ (mean difference) | | | 0.93 |
| $S_D$ | | | 0.42 |
| t-value | | | 6.94 |
| t-value > 1.833 | | | Significant difference |

Intercourse in General Score

Conclusion:

The results show a mean improvement of 0.9 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (LP) | 3.00 | 4.00 | 1.00 |
| 2 (IM) | 3.00 | 4.00 | 1.00 |
| 3 (SR) | 3.00 | 4.00 | 1.00 |
| 4 (BL) | 3.00 | 4.00 | 1.00 |
| 5 (DS) | 2.67 | 4.00 | 1.33 |
| 6 (KA) | 2.33 | 3.00 | 0.67 |
| 7 (MR) | 2.67 | 4.00 | 1.33 |
| 8 (TC) | 3.00 | 4.00 | 1.00 |
| 9 (LR) | 2.33 | 3.00 | 0.67 |
| 10 (HN) | 1.00 | 2.00 | 1.00 |
| SUM (X − Y) | | | 10.00 |
| $\overline{D}$ (mean difference) | | | 1.0 |
| $S_D$ | | | 0.44 |
| t-value | | | 7.12 |
| t-value > 1.833 | | | Significant difference |

Example 1c—Results of Homosexual Females

Sexual Arousal Score

Conclusion:

The results show a mean improvement of 1.6 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (KL) | 3.67 | 5.00 | 1.33 |
| 2 (LN) | 3.00 | 5.00 | 2.00 |
| 3 (CF) | 2.00 | 5.00 | 3.00 |
| 4 (EM) | 3.00 | 5.00 | 2.00 |
| 5 (JS) | 3.00 | 3.00 | 0.00 |
| 6 (FW) | 2.67 | 5.00 | 2.33 |
| 7 (MB) | 3.00 | 3.00 | 0.00 |
| 8 (EP) | 3.67 | 5.00 | 1.33 |
| 9 (AS) | 3.00 | 5.00 | 2.00 |
| 10 (VT) | 3.00 | 5.00 | 2.00 |
| SUM (X − Y) | | | 16.0 |
| $\overline{D}$ (mean difference) | | | 1.60 |
| $S_D$ | | | 1.33 |
| t-value | | | 3.78 |
| t-value > 1.833 | | | Significant difference |

Lubrication Score

Conclusion: The results show a mean improvement of 1.5 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (KL) | 3.67 | 5.00 | 1.33 |
| 2 (LN) | 3.00 | 5.00 | 2.00 |
| 3 (CF) | 2.33 | 5.00 | 2.67 |
| 4 (EM) | 3.00 | 5.00 | 2.00 |
| 5 (JS) | 3.00 | 3.00 | 0.00 |
| 6 (FW) | 2.67 | 5.00 | 2.33 |
| 7 (MB) | 3.67 | 3.00 | −0.67 |
| 8 (EP) | 3.67 | 5.00 | 1.33 |
| 9 (AS) | 3.00 | 5.00 | 2.00 |
| 10 (VT) | 3.00 | 5.00 | 2.00 |
| SUM (X − Y) | | | 15.0 |
| $\overline{D}$ (mean difference) | | | 1.50 |
| $S_D$ | | | 1.40 |
| t-value | | | 3.39 |
| t-value > 1.833 | | | Significant difference |

Orgasm Score

Conclusion:

The results show a mean improvement of 1.9 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (KL) | 2.67 | 4.00 | 1.33 |
| 2 (LN) | 3.00 | 5.00 | 2.00 |
| 3 (CF) | 1.33 | 4.00 | 2.67 |
| 4 (EM) | 2.00 | 5.00 | 3.00 |
| 5 (JS) | 2.00 | 2.00 | 0.00 |
| 6 (FW) | 2.00 | 4.00 | 2.00 |
| 7 (MB) | 2.00 | 2.00 | 0.00 |
| 8 (EP) | 2.67 | 5.00 | 2.33 |
| 9 (AS) | 2.00 | 4.00 | 2.00 |
| 10 (VT) | 2.00 | 4.67 | 2.67 |
| SUM (X − Y) | | | 18.0 |
| $\overline{D}$ (mean difference) | | | 1.80 |
| $S_D$ | | | 1.51 |
| t-value | | | 3.78 |
| t-value > 1.833 | | | Significant difference |

Emotional Satisfaction Score

Conclusion:

The results show a mean improvement of 1.1 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (KL) | 3.33 | 4.00 | 0.67 |
| 2 (LN) | 3.00 | 4.00 | 1.00 |
| 3 (CF) | 2.33 | 4.00 | 1.67 |
| 4 (EM) | 3.00 | 4.00 | 1.00 |
| 5 (JS) | 2.33 | 3.00 | 0.67 |
| 6 (FW) | 2.33 | 4.00 | 1.67 |
| 7 (MB) | 3.00 | 4.00 | 1.00 |
| 8 (EP) | 3.00 | 4.00 | 1.00 |
| 9 (AS) | 2.33 | 4.00 | 1.67 |
| 10 (VT) | 3.00 | 4.00 | 1.00 |
| SUM (X − Y) | | | 11.4 |
| $\overline{D}$ (mean difference) | | | 1.14 |
| $S_D$ | | | 0.74 |
| t-value | | | 4.88 |
| t-value > 1.833 | | | Significant difference |

Discomfort During Penetration Score

Conclusion:

The results show a mean improvement of 1.0 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (KL) | 3.67 | 5.00 | 1.33 |
| 2 (LN) | 4.00 | 5.00 | 1.00 |
| 3 (CF) | 3.33 | 5.00 | 1.67 |
| 4 (EM) | 4.00 | 5.00 | 1.00 |
| 5 (JS) | 4.00 | 4.00 | 0.00 |
| 6 (FW) | 3.33 | 5.00 | 1.67 |
| 7 (MB) | 4.00 | 4.00 | 0.00 |
| 8 (EP) | 4.33 | 5.00 | 0.67 |
| 9 (AS) | 3.00 | 5.00 | 2.00 |
| 10 (VT) | 4.00 | 5.00 | 1.00 |
| | SUM (X − Y) | | 10.3 |
| | $\overline{D}$ (mean difference) | | 1.03 |
| | $S_D$ | | 0.95 |
| | t-value | | 3.43 |
| | t-value > 1.833 | | Significant difference |

Intercourse in General Score

Conclusion:

The results show a mean improvement of 1.1 point (on a 1-5 scale), which is statistically significant (P<0.05).

Detailed Results:

| Individual | Placebo score (Y) Mean of 3 tests | Treatment score (X) Mean of 3 tests | X − Y |
|---|---|---|---|
| 1 (KL) | 2.67 | 4.00 | 1.33 |
| 2 (LN) | 2.00 | 4.00 | 2.00 |
| 3 (CF) | 2.33 | 4.00 | 1.67 |
| 4 (EM) | 3.00 | 4.00 | 1.00 |
| 5 (JS) | 3.00 | 3.00 | 0.00 |
| 6 (FW) | 2.33 | 4.00 | 1.67 |
| 7 (MB) | 3.00 | 3.00 | 0.00 |
| 8 (EP) | 3.33 | 4.00 | 0.67 |
| 9 (AS) | 2.67 | 4.00 | 1.33 |
| 10 (VT) | 3.00 | 4.00 | 1.00 |
| | SUM (X − Y) | | 10.7 |
| | $\overline{D}$ (mean difference) | | 1.07 |
| | $S_D$ | | 0.87 |
| | t-value | | 3.86 |
| | t-value > 1.833 | | Significant difference |

General Observations After Example 1

All participants responded positively to the trial formulation and the effect of the trial formulation is statistically significantly different from placebo. The test treatment was responded significantly to by approximately 80% of the trial subject, whereas approx. 20% of the trial subjects experienced only minor improvements. These latter participants were, although a slight positive response was observed, classified as functionally "non-responders" (males (2/10), females (5/20)).

Example 2—Composition Comparison

Formulation A:

Responders:

On average approx. 80% of trial subjects in example 2 responded significantly on test formulation A, whereas 20% showed only minor improvements. No subjects showed a decreased sexual experience. These results confirm the findings of example 1. Non-responders to Formula A were also non-responders to all other formulations.

| | Responders | Non-responders | % responders |
|---|---|---|---|
| Male | 5.0 | 1.0 | 83% |
| Female (all) | 14.0 | 4.0 | 78% |
| Heterosexual female | 4.0 | 2.0 | 67% |
| Homosexual females | 19.0 | 5.0 | 79% |

Effect:

Disregarding the non-responders, the effect of formulation A was very pronounced as seen in the tables below wherein the numbers represent average questionnaire scores for responders:

| Male responders | Formulation A | Normal |
|---|---|---|
| Sexual arousal | 4.9 | 2.0 |
| Erection hardness | 5.0 | 2.0 |
| desensitivity to penis | 4.8 | 2.0 |
| Emotional satisfaction | 4.6 | 2.0 |
| Intercourse in general | 4.8 | 2.0 |
| Average score | 4.8 | 2.0 |
| IELT | 707.6 (sec) | (392 average placebo IELT in example 1 trial) |

| Heterosexual female responders | Formulation A | Normal |
|---|---|---|
| Sexual arousal | 5.0 | 2.0 |
| Lubrication | 4.8 | 2.0 |
| Orgasm | 4.2 | 2.0 |
| Emotional satisfaction | 4.7 | 2.0 |
| Intercourse in general | 4.7 | 2.0 |
| Average score | 4.7 | 2.0 |

| Homosexual female responders | Formulation A | Normal |
|---|---|---|
| Sexual arousal | 4.9 | 2.0 |
| Lubrication | 4.8 | 2.0 |
| Orgasm | 4.6 | 2.0 |
| Emotional satisfaction | 4.9 | 2.0 |
| Intercourse in general | 4.8 | 2.0 |
| Average score | 4.8 | 2.0 |

Formulation (Formula) A Vs. Other Formulations

| Formulation comparison Average score | Male | Female (all) | Hetero female |
|---|---|---|---|
| Form A | 4.8 | 4.9 | 4.8 | 4.7 |
| Form B | 3.8 | 4.0 | 3.7 | 3.6 |
| Form C | 3.1 | 3.3 | 3.1 | 3.3 |
| Form D | 4.7 | 4.9 | 4.7 | 4.5 |
| Form E | 3.0 | 3.0 | 3.0 | 3.0 |
| Form F | 2.9 | 3.0 | 2.9 | 3.0 |
| Form G | 2.9 | 2.9 | 3.0 | 3.0 |

For responders, the result show that all formulations are significantly better that "Normal", i.e. that all formulations are effective. However, Formulas A an D is better than formula B, and formulae B is better than formulas C, E, F and G.

Comparing formula A vs. formula E, F and G shows that the presence of substantial amounts of arginine (at least 4.0 g) is preferred and that the thereby obtained effect cannot be substituted by increasing the amounts of citrulline.

Comparing formula A vs. formula C shows that the presence of citrulline (at least 1.0 g) is preferred and that the thereby obtained effect cannot be substituted by increasing the amounts of arginine.

Comparing formula A vs. formula B shows that the presence of proanthocyanidins is highly preferred.

Comparing formula A vs. formula D shows that the increase of citrulline (to least 2.0 g) does not result in significantly better effect.

Collectively, these results show that the presence of both arginine and citrulline in effective formulations is preferred, with arginine being in excess of citrulline; arginine should preferably be present at least 4 g, preferably at 6 g; citrulline should preferably be present at at least 1 g, preferably at 1.5 g; proanthocyanidins should preferably be present (the amount of which may be lowered as this ingredient is believed to be relevant as a catalyst only).

Raw Data:

The below tables show the results of the trial in example 2 (the parenthesis shows trial couple no, sex, initials, partner sex). Trial subject (1, M, BG, F) is therefore from trial couple 1, male, initials BG, and his partner is female).

| Trial couple | A | A | B | B | E | E | N | N |
|---|---|---|---|---|---|---|---|---|
| (1, M, BG, F) | | | | | | | | |
| Sexual arousal score | 5 | 5 | 4 | 4 | 3 | 3 | 2 | 2 |
| IELT (sec.) | 688 | 701 | 612 | 619 | 402 | 415 | | |
| Erection hardness | 5 | 5 | 4 | 4 | 3 | 3 | 2 | 2 |
| desensitivity to penis | 5 | 5 | 4 | 4 | 3 | 3 | 2 | 2 |
| Emotional satisfaction | 5 | 5 | 4 | 4 | 3 | 3 | 2 | 2 |
| Intercourse ingeneral | 5 | 5 | 4 | 4 | 3 | 3 | 2 | 2 |
| (1, F, HG, M)) | | | | | | | | |
| Sexual arousal score | 5 | 5 | 4 | 4 | 3 | 3 | 2 | 2 |
| Lubrication score | 5 | 5 | 4 | 4 | 3 | 3 | 2 | 2 |
| Orgasm Score | 4 | 4 | 3 | 3 | 3 | 3 | 2 | 2 |
| Emotional satisfaction | 5 | 5 | 4 | 4 | 3 | 3 | 2 | 2 |
| Intercourse ingeneral | 5 | 5 | 4 | 4 | 3 | 3 | 2 | 2 |
| (2, M, DA, F) | | | | | | | | |
| Sexual arousal score | 2 | 2 | 2 | 2 | 2 | 2 | 2 | 2 |
| IELT (sec.) | 356 | 351 | 339 | 343 | 329 | 334 | | 2 |
| Erection hardness | 2 | 2 | 2 | 2 | 2 | 2 | 2 | 2 |
| desensitivity to penis | 2 | 2 | 2 | 2 | 2 | 2 | 2 | 2 |
| Emotional satisfaction | 2 | 2 | 2 | 2 | 2 | 2 | 2 | 2 |
| Intercourse ingeneral | 2 | 2 | 2 | 2 | 2 | 2 | 2 | 2 |
| (2, F, SH, M) | | | | | | | | |
| Sexual arousal score | 5 | 5 | 4 | 4 | 3 | 3 | 2 | 2 |
| Lubrication score | 5 | 5 | 3 | 3 | 3 | 3 | 2 | 2 |
| Orgasm Score | 4 | 4 | 3 | 3 | 3 | 3 | 2 | 2 |
| Emotional satisfaction | 4 | 4 | 3 | 4 | 3 | 3 | 2 | 2 |
| Intercourse ingeneral | 4 | 4 | 3 | 3 | 3 | 3 | 2 | 2 |
| (7, F, EV, F) | | | | | | | | |
| Sexual arousal score | 5 | 5 | 4 | 4 | 3 | 3 | 2 | 2 |
| Lubrication score | 5 | 5 | 4 | 4 | 3 | 3 | 2 | 2 |
| Orgasm Score | 5 | 4 | 3 | 4 | 3 | 3 | 2 | 2 |
| Emotional satisfaction | 5 | 5 | 3 | 4 | 4 | 3 | 2 | 2 |
| Intercourse ingeneral | 5 | 4 | 4 | 4 | 3 | 3 | 2 | 2 |
| (7, F, NS, F) | | | | | | | | |
| Sexual arousal score | 5 | 5 | 4 | 4 | 3 | 3 | 2 | 2 |
| Lubrication score | 5 | 5 | 4 | 4 | 3 | 3 | 2 | 2 |
| Orgasm Score | 5 | 5 | 3 | 3 | 3 | 3 | 2 | 2 |
| Emotional satisfaction | 5 | 5 | 4 | 4 | 4 | 3 | 2 | 2 |
| Intercourse ingeneral | 5 | 5 | 3 | 4 | 3 | 3 | 2 | 2 |
| (8, F, AH, F) | | | | | | | | |
| Sexual arousal score | 5 | 5 | 5 | 4 | 2 | 3 | 2 | 2 |
| Lubrication score | 5 | 5 | 4 | 3 | 3 | 3 | 2 | 2 |
| Orgasm Score | 5 | 4 | 3 | 4 | 3 | 3 | 2 | 2 |
| Emotional satisfaction | 5 | 5 | 4 | 3 | 2 | 3 | 2 | 2 |
| Intercourse ingeneral | 5 | 5 | 4 | 4 | 3 | 3 | 2 | 2 |
| (8, F, CW, F) | | | | | | | | |
| Sexual arousal score | 4 | 5 | 4 | 4 | 3 | 3 | 2 | 2 |
| Lubrication score | 5 | 5 | 3 | 4 | 3 | 3 | 2 | 2 |
| Orgasm Score | 4 | 4 | 4 | 3 | 3 | 3 | 2 | 2 |
| Emotional satisfaction | 4 | 5 | 4 | 4 | 3 | 3 | 2 | 2 |
| Intercourse ingeneral | 4 | 5 | 4 | 4 | 3 | 3 | 2 | 2 |

-continued

| Trial couple | A | A | C | C | F | F | N | N |
|---|---|---|---|---|---|---|---|---|
| (3, M, AS, F) | | | | | | | | |
| Sexual arousal score | 5 | 5 | 4 | 4 | 3 | 3 | 2 | 2 |
| IELT (sec.) | 766 | 759 | 492 | 504 | 436 | 424 | | |
| Erection hardness | 5 | 5 | 4 | 4 | 3 | 3 | 2 | 2 |
| desensitivity to penis | 5 | 5 | 3 | 4 | 3 | 3 | 2 | 2 |
| Emotional satisfaction | 5 | 5 | 3 | 4 | 3 | 3 | 2 | 2 |
| Intercourse ingeneral | 5 | 5 | 3 | 3 | 3 | 3 | 2 | 2 |
| (3, F, SG, M)) | | | | | | | | |
| Sexual arousal score | 5 | 5 | 3 | 4 | 3 | 3 | 2 | 2 |
| Lubrication score | 4 | 5 | 4 | 4 | 3 | 3 | 2 | 2 |
| Orgasm Score | 4 | 5 | 3 | 3 | 3 | 3 | 2 | 2 |
| Emotional satisfaction | 5 | 5 | 3 | 3 | 3 | 3 | 2 | 2 |
| Intercourse ingeneral | 5 | 5 | 3 | 3 | 3 | 3 | 2 | 2 |
| (4, M, MH, F) | | | | | | | | |
| Sexual arousal score | 5 | 5 | 3 | 3 | 3 | 3 | 2 | 2 |
| IELT (sec.) | 709 | 728 | 457 | 444 | 405 | 426 | | |
| Erection hardness | 5 | 5 | 3 | 3 | 3 | 3 | 2 | 2 |
| desensitivity to penis | 4 | 5 | 3 | 3 | 3 | 3 | 2 | 2 |
| Emotional satisfaction | 4 | 4 | 3 | 3 | 3 | 3 | 2 | 2 |
| Intercourse ingeneral | 4 | 4 | 3 | 3 | 3 | 3 | 2 | 2 |
| (4, F, NM, M) | | | | | | | | |
| Sexual arousal score | 3 | 3 | 2 | 2 | 2 | 2 | 2 | 2 |
| Lubrication score | 2 | 2 | 2 | 2 | 2 | 2 | 2 | 2 |
| Orgasm Score | 2 | 2 | 2 | 2 | 2 | 2 | 2 | 2 |
| Emotional satisfaction | 3 | 2 | 2 | 2 | 2 | 2 | 2 | 2 |
| Intercourse ingeneral | 2 | 2 | 2 | 2 | 2 | 2 | 2 | 2 |
| (9, F, BC, F) | | | | | | | | |
| Sexual arousal score | 2 | 3 | 2 | 2 | 2 | 2 | 2 | 2 |
| Lubrication score | 3 | 2 | 2 | 2 | 2 | 2 | 2 | 2 |
| Orgasm Score | 2 | 2 | 2 | 2 | 2 | 2 | 2 | 2 |
| Emotional satisfaction | 2 | 2 | 2 | 2 | 2 | 2 | 2 | 2 |
| Intercourse ingeneral | 2 | 2 | 2 | 2 | 2 | 2 | 2 | 2 |
| (9, F, MK, F) | | | | | | | | |
| Sexual arousal score | 5 | 5 | 3 | 3 | 3 | 3 | 2 | 2 |
| Lubrication score | 5 | 5 | 3 | 2 | 3 | 3 | 2 | 2 |
| Orgasm Score | 5 | 5 | 3 | 3 | 3 | 3 | 2 | 2 |
| Emotional satisfaction | 5 | 4 | 2 | 3 | 3 | 2 | 2 | 2 |
| Intercourse ingeneral | 4 | 4 | 2 | 3 | 3 | 2 | 2 | 2 |
| (10, F, JW, F) | | | | | | | | |
| Sexual arousal score | 4 | 5 | 3 | 3 | 3 | 3 | 2 | 2 |
| Lubrication score | 5 | 5 | 3 | 4 | 2 | 2 | 2 | 2 |
| Orgasm Score | 5 | 5 | 3 | 3 | 3 | 2 | 2 | 2 |
| Emotional satisfaction | 5 | 5 | 3 | 4 | 3 | 3 | 2 | 2 |
| Intercourse ingeneral | 5 | 5 | 3 | 3 | 3 | 3 | 2 | 2 |
| (10, F, TC, F) | | | | | | | | |
| Sexual arousal score | 5 | 5 | 3 | 4 | 4 | 3 | 2 | 2 |
| Lubrication score | 5 | 5 | 3 | 3 | 3 | 3 | 2 | 2 |
| Orgasm Score | 4 | 5 | 2 | 3 | 3 | 3 | 2 | 2 |
| Emotional satisfaction | 5 | 5 | 3 | 4 | 3 | 3 | 2 | 2 |
| Intercourse ingeneral | 5 | 5 | 3 | 3 | 3 | 3 | 2 | 2 |

| Trial couple | A | A | D | D | G | G | N | N |
|---|---|---|---|---|---|---|---|---|
| (5, M, JC, F) | | | | | | | | |
| Sexual arousal score | 5 | 4 | 5 | 5 | 3 | 3 | 2 | 2 |
| IELT (sec.) | 685 | 681 | 694 | 699 | 451 | 443 | | |
| Erection hardness | 5 | 5 | 5 | 5 | 3 | 3 | 2 | 2 |
| desensitivity to penis | 5 | 5 | 5 | 5 | 2 | 3 | 2 | 2 |
| Emotional satisfaction | 5 | 5 | 5 | 5 | 3 | 3 | 2 | 2 |
| Intercourse ingeneral | 5 | 5 | 5 | 5 | 3 | 3 | 2 | 2 |
| (5, F, ML, M)) | | | | | | | | |
| Sexual arousal score | 4 | 5 | 5 | 4 | 3 | 3 | 2 | 2 |
| Lubrication score | 4 | 5 | 5 | 4 | 3 | 3 | 2 | 2 |
| Orgasm Score | 4 | 5 | 4 | 4 | 3 | 3 | 2 | 2 |
| Emotional satisfaction | 4 | 5 | 5 | 5 | 3 | 3 | 2 | 2 |
| Intercourse ingeneral | 4 | 5 | 5 | 4 | 3 | 3 | 2 | 2 |

(6, M, CH, F)

| | | | | | | | | |
|---|---|---|---|---|---|---|---|---|
| Sexual arousal score | 5 | 5 | 5 | 5 | 3 | 2 | 2 | 2 |
| IELT (sec.) | 681 | 678 | 692 | 696 | 417 | 405 | | |
| Erection hardness | 5 | 5 | 5 | 5 | 3 | 3 | 2 | 2 |
| desensitivity to penis | 5 | 4 | 5 | 5 | 3 | 3 | 2 | 2 |
| Emotional satisfaction | 4 | 4 | 4 | 5 | 4 | 3 | 2 | 2 |
| Intercourse ingeneral | 5 | 5 | 5 | 5 | 3 | 3 | 2 | 2 |

(6, F, SN, M)

| | | | | | | | | |
|---|---|---|---|---|---|---|---|---|
| Sexual arousal score | 2 | 3 | 3 | 2 | 2 | 2 | 2 | 2 |
| Lubrication score | 2 | 2 | 3 | 3 | 2 | 2 | 2 | 2 |
| Orgasm Score | 2 | 2 | 2 | 2 | 2 | 2 | 2 | 2 |
| Emotional satisfaction | 3 | 2 | 3 | 3 | 2 | 2 | 2 | 2 |
| Intercourse ingeneral | 2 | 2 | 3 | 3 | 2 | 2 | 2 | 2 |

(11, F, CJ, F)

| | | | | | | | | |
|---|---|---|---|---|---|---|---|---|
| Sexual arousal score | 5 | 5 | 5 | 5 | 3 | 3 | 2 | 2 |
| Lubrication score | 4 | 4 | 5 | 4 | 3 | 2 | 2 | 2 |
| Orgasm Score | 4 | 4 | 4 | 4 | 2 | 2 | 2 | 2 |
| Emotional satisfaction | 5 | 5 | 5 | 5 | 3 | 3 | 2 | 2 |
| Intercourse ingeneral | 5 | 5 | 5 | 5 | 3 | 3 | 2 | 2 |

(11, F, MD, F)

| | | | | | | | | |
|---|---|---|---|---|---|---|---|---|
| Sexual arousal score | 5 | 5 | 5 | 5 | 3 | 2 | 2 | 2 |
| Lubrication score | 5 | 4 | 5 | 5 | 3 | 3 | 2 | 2 |
| Orgasm Score | 5 | 4 | 5 | 4 | 3 | 3 | 2 | 2 |
| Emotional satisfaction | 5 | 5 | 5 | 5 | 3 | 4 | 2 | 2 |
| Intercourse ingeneral | 5 | 5 | 5 | 5 | 3 | 3 | 2 | 2 |

(12, F, LP, F)

| | | | | | | | | |
|---|---|---|---|---|---|---|---|---|
| Sexual arousal score | 5 | 5 | 5 | 5 | 3 | 3 | 2 | 2 |
| Lubrication score | 5 | 4 | 4 | 5 | 3 | 3 | 2 | 2 |
| Orgasm Score | 5 | 5 | 5 | 4 | 3 | 3 | 2 | 2 |
| Emotional satisfaction | 5 | 4 | 5 | 4 | 3 | 4 | 2 | 2 |
| Intercourse ingeneral | 5 | 5 | 5 | 4 | 3 | 3 | 2 | 2 |

(12, F, VH, F)

| | | | | | | | | |
|---|---|---|---|---|---|---|---|---|
| Sexual arousal score | 3 | 2 | 3 | 2 | 2 | 2 | 2 | 2 |
| Lubrication score | 3 | 2 | 3 | 3 | 2 | 2 | 2 | 2 |
| Orgasm Score | 3 | 2 | 2 | 2 | 2 | 2 | 2 | 2 |
| Emotional satisfaction | 3 | 3 | 3 | 2 | 2 | 2 | 2 | 2 |
| Intercourse ingeneral | 2 | 2 | 3 | 2 | 2 | 2 | 2 | 2 |

Paired t test performed.

We interpret $\mu_D=0$ as indicating that the mean improvement of the two formulations are the same and $\mu_D>0$ as indicating the mean response of the INXO formulation is higher than the comparison formulation.

Test of the null hypothesis $H_0: \mu_D = \mu_{D,0}$ are based on the ratio $$t = \frac{\overline{D} - u_D}{s_D/\sqrt{n}}$$

where $\overline{D}$ and $S_D^2$ is given by:

$$\overline{D} = \frac{\sum_{i}^{n} D_i}{n}, \quad S_D^2 = \frac{\sum_{i}^{n}(D_i - \overline{D})^2}{n-1}$$

1. Null hypothesis: $\mu_D=0$, alternative hypothesis $\mu_D>0$
2. Level of significance: $\alpha$
3. Criterion: Reject the null hypothesis if $t >$ the value of $t_\alpha$ for $v$ degrees of freedom (n−1).

Formulation A Vs Formulation B (Inxo Vs No Pygnogenol)

An average score for INXO and Formulation B was calculated based on the individual scores in sexual arousal score, emotional satisfaction score, intercourse in general score, erection hardness score and de-sensitivity to penis score for males and an average score based on the individual scores in sexual arousal score, emotional satisfaction score, intercourse in general score, lubrication score, discomfort during penetration score and orgasm score for females.

Detailed Results:

| Individual | Average score Formulation A ($X_i$) | Average score Formulation B ($Y_i$) | $X_i - Y_i$ |
|---|---|---|---|
| 1 (BG) | 5.0 | 4.0 | 1.0 |
| 2 (HG) | 4.8 | 3.8 | 1.0 |
| 3 (DA) | 2.0 | 2.0 | 0 |
| 4 (SH) | 4.4 | 3.3 | 1.1 |
| 5 (EV) | 4.8 | 3.8 | 1.0 |
| 6 (NS) | 5.0 | 3.7 | 1.3 |
| 7 (AH) | 4.9 | 3.8 | 1.1 |
| 8 (CW) | 4.5 | 3.8 | 0.7 |
| | SUM (X − Y) | | 7.2 |
| | $\overline{D}$ (mean difference) | | 0.9 |
| | $S_D$ | | 0.4 |
| | t-value | | 6.4 | t-value > 3.449, for $\alpha = 0.005$ and 7 degrees of freedom. Null hypothesis rejected
Conclusion: Significant difference. Formulation A is better than formulation B with 99.5% probability. There is 0.5% chance that a type 1 error occurred and that Formulation A is not better than formulation B.

Formulation A vs Formulation C (Inxo vs 7.5 g Arginine)

An average score for INXO and Formulation C was calculated based on the individual scores in sexual arousal score, emotional satisfaction score, intercourse in general score, erection hardness score and de-sensitivity to penis score for males and an average score based on the individual scores in sexual arousal score, emotional satisfaction score, intercourse in general score, lubrication score, discomfort during penetration score and orgasm score for females.

Detailed Results:

| Individual | Average score Formulation A ($X_i$) | Average score Formulation C ($Y_i$) | $X_i - Y_i$ |
|---|---|---|---|
| 1 (AS) | 5.0 | 3.6 | 1.4 |
| 2 (SG) | 4.8 | 3.3 | 1.5 |
| 3 (MH) | 4.5 | 3.0 | 1.5 |
| 4 (NM) | 2.3 | 2.0 | 0.3 |
| 5 (BC) | 2.2 | 2.0 | 0.2 |
| 6 (MK) | 4.7 | 2.7 | 2.0 |
| 7 (JW) | 4.9 | 3.2 | 1.7 |
| 8 (TC) | 4.9 | 3.1 | 1.8 |
| SUM (X − Y) | | | 10.4 |
| $\bar{D}$ (mean difference) | | | 1.3 |
| $S_D$ | | | 0.7 |
| t-value | | | 5.4 | t-value > 3.499, for α = 0.01 and 7 degrees of freedom. Null hypothesis rejected.
Conclusion: Significant difference. Formulation A is better than formulation C with 99.5% probability. There is 0.5% probability that a type I error occurred and that Formulation A is not better than formulation C.

Formulation A Vs Formulation D (Inxo Vs. Extra Citrulline)

An average score for INXO and Formulation D was calculated based on the individual scores in sexual arousal score, emotional satisfaction score, intercourse in general score, erection hardness score and de-sensitivity to penis score for males and an average score based on the individual scores in sexual arousal score, emotional satisfaction score, intercourse in general score, lubrication score, discomfort during penetration score and orgasm score for females.

Detailed Results:

| Individual | Average score Formulation D ($X_i$) | Average score Formulation A ($X_i$) | $X_i - Y_i$ |
|---|---|---|---|
| 1 (JC) | 5.0 | 4.9 | 0.1 |
| 2 (ML) | 4.5 | 4.5 | 0 |
| 3 (CH) | 4.9 | 4.7 | 0.2 |
| 4 (SN) | 2.7 | 2.2 | 0.5 |
| 5 (CJ) | 4.7 | 4.6 | 0.1 |
| 6 (MD) | 4.9 | 4.8 | 0.1 |
| 7 (LP) | 4.6 | 4.8 | −0.2 |
| 8 (VH) | 2.5 | 2.5 | 0 |
| SUM (X−Y) | | | 0.8 |
| $\bar{D}$ (mean difference) | | | 0.1 |
| $S_D$ | | | 0,2 |
| t-value | | | 1,41 | t-value > 1.415, for a = 0.10 and 7 degrees of freedom. Null hypothesis cannot be rejected.
Conclusion: Not significant. We cannot conclude with 90% probability that formulation D is better than Formaulation A.

Formulation A vs Formulation E (Inxo Vs. 7.5 Citrulline)

An average score for INXO and Formulation E was calculated based on the individual scores in sexual arousal score, emotional satisfaction score, intercourse in general score, erection hardness score and de-sensitivity to penis score for males and an average score based on the individual scores in sexual arousal score, emotional satisfaction score, intercourse in general score, lubrication score, discomfort during penetration score and orgasm score for females.

Detailed Results:

| Individual | Average score Formulation A ($X_i$) | Average score Formulation E ($X_i$) | $X_i - Y_i$ |
|---|---|---|---|
| 1 (BG) | 5.0 | 3.0 | 2 |
| 2 (HG) | 4.8 | 3.0 | 1.8 |
| 3 (DA) | 2.0 | 2.0 | 0 |
| 4 (SH) | 4.4 | 3.0 | 1.4 |
| 5 (EV) | 4.8 | 3.1 | 1.7 |
| 6 (NS) | 4.8 | 3.1 | 1.7 |
| 7 (AH) | 4.8 | 2.8 | 2 |
| 8 (CW) | 4.4 | 3.0 | 1.4 |
| SUM (X − Y) | | | 12 |
| $\bar{D}$ (mean difference) | | | 1.5 |
| $S_D$ | | | 0.65 |
| t-value | | | 6.5 | t-value > 3.499, for α = 0.005 and 7 degrees of freedom. Null hypothesis rejected.
Conclusion: Significant difference. Formulation A is better than formulation E with 99.5% probability. There is 0.5% probability that a type I error occurred and that Formulation A is not better than formulation E.

Formulation A vs Formulation F (Inxo Vs. Low Amount of Arginine)

An average score for INXO and Formulation F was calculated based on the individual scores in sexual arousal score, emotional satisfaction score, intercourse in general score, erection hardness score and de-sensitivity to penis score for males and an average score based on the individual scores in sexual arousal score, emotional satisfaction score, intercourse in general score, lubrication score, discomfort during penetration score and orgasm score for females.

Detailed Results:

| Individual | Average score Formulation A ($X_i$) | Average score Formulation F ($X_i$) | $X_i - Y_i$ |
|---|---|---|---|
| 1 (AS) | 5.0 | 3.0 | 2.0 |
| 2 (SG) | 4.8 | 3.0 | 1.8 |
| 3 (MH) | 4.5 | 3.0 | 1.5 |
| 4 (NM) | 2.3 | 2.0 | 0.3 |
| 5 (BC) | 2.2 | 2.0 | 0.2 |
| 6 (MK) | 4.6 | 2.8 | 1.8 |
| 7 (JW) | 4.9 | 2.8 | 2.1 |
| 8 (TC) | 4.9 | 3.1 | 1.8 |
| SUM (X − Y) | | | 11.5 |
| $\bar{D}$ (mean difference) | | | 1.4 |
| $S_D$ | | | 0.8 |
| t-value | | | 5.4 | t-value > 3.499, for α = 0.005 and 7 degrees of freedom. Null hypothesis rejected.
Conclusion: Significant difference. Formulation A is better than formulation F with 99.5% probability. There is 0.5% probability that a type I error occurred and that Formulation A is not better than formulation F.

Formulation A vs Formulation G (Inxo vs. More Citrulline Less Arginine)

An average score for INXO and Formulation G was calculated based on the individual scores in sexual arousal score, emotional satisfaction score, intercourse in general score, erection hardness score and de-sensitivity to penis score for males and an average score based on the individual scores in sexual arousal score, emotional satisfaction score, intercourse in general score, lubrication score, discomfort during penetration score and orgasm score for females.

Detailed Results:

| Individual | Average score Formulation A ($X_i$) | Average score Formulation G ($X_i$) | $X_i - Y_i$ |
|---|---|---|---|
| 1 (JC) | 4.9 | 2.9 | 2.0 |
| 2 (ML) | 4.5 | 3.0 | 1.5 |
| 3 (CH) | 4.7 | 3.0 | 1.7 |

-continued

| Individual | Average score Formulation A ($X_i$) | Average score Formulation G ($X_i$) | $X_i - Y_i$ |
|---|---|---|---|
| 4 (SN) | 2.2 | 2.0 | 0.2 |
| 5 (CJ) | 4.6 | 2.7 | 1.9 |
| 6 (MD) | 4.8 | 3.0 | 1.8 |
| 7 (LP) | 4.8 | 3.1 | 1.7 |
| 8 (VH) | 2.5 | 2.0 | 0.5 |
| | SUM (X − Y) | | 11.3 |
| | $\overline{D}$ (mean difference) | | 1.41 |
| | $S_D$ | | 0.68 |
| | t-value | | 5.9 | t-value > 3.499, for α = 0.005 and 7 degrees of freedom. Null hypothesis rejected.
Conclusion: Significant difference. Formulation A is better than formulation G with 99.5% probability. There is 0.5% probability that a type I error occurred and that Formulation A is not better than formulation G.

The invention claimed is:

1. A composition comprising L-arginine and L-citrulline or a physiologically acceptable salt or hydrate of any one thereof, wherein the composition is in a unit dosage form and wherein the content of L-arginine or a physiologically acceptable salt or hydrate thereof is at least 4.0 g and the content of L-citrulline or a physiologically acceptable salt or hydrate thereof is in the range from 1.1-3.0 g, wherein the composition comprises one or more proanthocyanidins.

2. A composition according to claim 1, wherein the content of L-arginine or a physiologically acceptable salt or hydrate thereof is in the range of from 4.0-10.0 g.

3. A composition according to claim 1, wherein the composition is in a unit dosage form for use on demand.

* * * * *